United States Patent
Li et al.

(10) Patent No.: US 6,514,983 B1
(45) Date of Patent: *Feb. 4, 2003

(54) COMPOUNDS, METHODS AND PHARMACEUTICAL COMPOSITIONS FOR TREATING NEURAL OR CARDIOVASCULAR TISSUE DAMAGE

(75) Inventors: Jia-He Li, Cockeysville, MD (US); Jie Zhang, Ellicott City, MD (US); Paul F. Jackson, Bel Air, MD (US); Keith M. Maclin, Baltimore, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/145,181

(22) Filed: Sep. 1, 1998

Related U.S. Application Data

(63) Continuation-in-part of application No. 09/047,502, filed on Mar. 25, 1998, now Pat. No. 6,306,889, which is a continuation-in-part of application No. 08/922,548, filed on Sep. 3, 1997, now Pat. No. 6,346,536.

(51) Int. Cl.[7] .................. A61K 31/47; C07D 217/22; C07D 217/18; C07D 401/04
(52) U.S. Cl. .................. 514/285; 514/183; 514/410; 546/61; 546/62; 546/66; 548/421
(58) Field of Search .................. 546/61, 62, 66; 514/183, 288, 298, 285, 410; 548/421

(56) References Cited

U.S. PATENT DOCUMENTS

| | | | |
|---|---|---|---|
| 932,290 A | 8/1909 | Kacer | 260/250 |
| 1,001,325 A | 8/1911 | Ullmann | 260/250 |
| 1,253,252 A | 1/1918 | Kardos et al. | 260/250 |
| 1,880,441 A | 10/1932 | Heidenreich et al. | |
| 1,895,105 A | 1/1933 | Rath et al. | |
| 2,467,692 A | 4/1949 | Petrow et al. | |
| 2,593,798 A | 4/1952 | Robinson | |
| 2,612,503 A | 9/1952 | Ullyot | |
| 2,638,472 A | 5/1953 | Grewe | |
| 2,666,059 A | 1/1954 | Davis et al. | |
| 2,700,040 A | 1/1955 | Ullyot | |
| 2,892,841 A | 6/1959 | Rudner | |
| 2,992,220 A | 7/1961 | Irving et al. | 260/288 |
| 3,247,212 A | 4/1966 | Johnson | |
| 3,291,801 A | 12/1966 | Montgomery | |
| 3,300,499 A | 1/1967 | Lesher et al. | |
| 3,403,157 A | 9/1968 | Humber et al. | 260/256.4 |
| 3,507,872 A | 4/1970 | Hegar | |
| 3,534,038 A | 10/1970 | Machatzke | 260/294.8 |
| 3,557,119 A | 1/1971 | Humber et al. | |
| 3,573,304 A | 3/1971 | Eberle et al. | 260/250 |
| 3,700,673 A | 10/1972 | Watson, Jr. | |
| 3,719,684 A | 3/1973 | Unger et al. | 260/294.8 |
| 3,723,436 A | 3/1973 | Hollstein et al. | |
| 3,759,924 A | 9/1973 | Jeanmart et al. | |
| 3,830,816 A | 8/1974 | Gittos et al. | |
| 3,838,134 A | 9/1974 | Glauthier | |

(List continued on next page.)

FOREIGN PATENT DOCUMENTS

| | | |
|---|---|---|
| BE | 562948 | 6/1960 |
| BE | 628255 | 5/1963 |
| CA | 1000701 | 11/1976 |

(List continued on next page.)

OTHER PUBLICATIONS

Simone, Oncology: Introduction, Cecil Textbook of Medicine, 20th Edition, vol. 1, pp. 1004–1010, 1996.*

Layzer, Section Five—Degenerative Diseases of the Nervous System, Cecil Textbook of Medicine, 20th Edition, vol. 2, pp. 2050–2057, 1996.*

(List continued on next page.)

Primary Examiner—Deepak R. Rao
(74) Attorney, Agent, or Firm—Nixon & Vanderhye P.C.

(57) ABSTRACT

This invention relates to compounds, pharmaceutical compositions, and methods of using compounds of the formula:

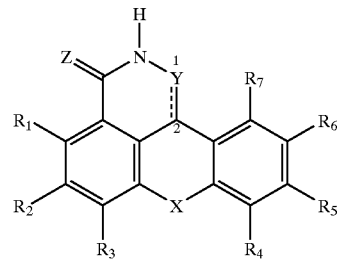

or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

X is $NR_{16}$, O, S, $CR_{12}R_{13}$, C=O, a bond, $-CR_{12}=CR_{13}-$, $-C(R_{12}R_{13})C(R_{14}R_{15})-$, or;

Rhd 1, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl.

21 Claims, 2 Drawing Sheets

U.S. PATENT DOCUMENTS

| | | | |
|---|---|---|---|
| 3,899,529 A | 8/1975 | Witzel | 260/517 |
| 3,900,477 A | 8/1975 | Philipp et al. | |
| 3,904,671 A | 9/1975 | Minatoya | |
| 3,932,643 A | 1/1976 | Gauthier | |
| 3,950,343 A | 4/1976 | Philipp et al. | |
| 3,978,066 A | 8/1976 | Philipp et al. | |
| 3,991,064 A | 11/1976 | Brown et al. | |
| 4,031,097 A | 6/1977 | Bach et al. | |
| 4,082,741 A | 4/1978 | Hunger et al. | |
| 4,169,897 A | 10/1979 | Meyer et al. | |
| 4,218,453 A | 8/1980 | Hannart | 424/256 |
| 4,309,543 A | 1/1982 | Keeley | 546/76 |
| 4,382,943 A | 5/1983 | Winter et al. | |
| RE31,617 E | 6/1984 | Beverung, Jr. et al. | |
| 4,472,401 A | 9/1984 | Kennewell et al. | |
| 4,594,415 A | 6/1986 | Robins et al. | |
| 4,639,454 A | 1/1987 | Hesson | 514/259 |
| 4,740,581 A | 4/1988 | Pruett et al. | 528/289 |
| 4,742,171 A | 5/1988 | Martin et al. | |
| 4,902,695 A | 2/1990 | Ornstein | 514/307 |
| 4,902,798 A | 2/1990 | Nakamatsu et al. | 546/76 |
| 4,925,968 A | 5/1990 | Sestanj et al. | 560/21 |
| 5,032,617 A | 7/1991 | Lee et al. | 514/617 |
| 5,041,653 A | 8/1991 | Lee et al. | 564/74 |
| 5,077,035 A | 12/1991 | Wieland et al. | 424/1.1 |
| 5,177,075 A | 1/1993 | Suto et al. | |
| 5,215,738 A | 6/1993 | Lee et al. | 424/10 |
| 5,262,564 A | 11/1993 | Kun et al. | |
| 5,274,097 A | 12/1993 | Schohe et al. | |
| 5,338,851 A | 8/1994 | Huff et al. | 546/141 |
| 5,391,376 A | 2/1995 | Long, Jr. et al. | |
| 5,391,554 A | 2/1995 | Showalter | |
| 5,395,835 A | 3/1995 | Glase et al. | 514/254 |
| 5,414,001 A | 5/1995 | Ireland et al. | |
| 5,420,136 A | 5/1995 | Lewis et al. | |
| 5,434,188 A | 7/1995 | Boschelli et al. | 514/617 |
| 5,464,871 A | 11/1995 | Kun et al. | |
| 5,473,074 A | 12/1995 | Kun et al. | |
| 5,480,631 A | 1/1996 | De Paulis et al. | |
| 5,482,975 A | 1/1996 | Kun et al. | |
| 5,516,941 A | 5/1996 | Kun et al. | |
| 5,587,384 A | 12/1996 | Zhang et al. | |
| 5,589,483 A | 12/1996 | West | 514/310 |
| 5,618,813 A | 4/1997 | Chu et al. | |
| 5,633,282 A | 5/1997 | Collins et al. | |
| 5,635,506 A | 6/1997 | Alberts et al. | 514/232.8 |
| 5,652,260 A | 7/1997 | Kun et al. | |
| 5,652,367 A | 7/1997 | Kun et al. | |
| 5,656,638 A | 8/1997 | Gaeta et al. | |
| 5,659,082 A | 8/1997 | Flitter et al. | |
| 5,665,710 A | 9/1997 | Rahman et al. | 514/44 |
| 5,670,518 A | 9/1997 | Kun et al. | |
| 5,703,089 A | 12/1997 | Brana et al. | 514/284 |
| 5,703,116 A | 12/1997 | Gaeta et al. | |
| 5,719,151 A | 2/1998 | Shall et al. | 514/248 |
| 5,753,674 A | 5/1998 | Kun et al. | |
| 5,756,510 A | 5/1998 | Griffin et al. | |
| 5,760,062 A | 6/1998 | Gaeta et al. | |
| 5,767,135 A | 6/1998 | Fernandez-Pol | 514/354 |
| RE36,397 E | 11/1999 | Zhang et al. | |
| 6,121,278 A | 9/2000 | Jackson et al. | |
| 6,197,785 B1 | 3/2001 | Jackson et al. | |
| 6,201,020 B1 | 3/2001 | Zhang | |
| 6,235,748 B1 | 5/2001 | Li et al. | |
| 6,291,425 B1 | 9/2001 | Li et al. | |
| 6,306,889 B1 | 10/2001 | Li et al. | |

FOREIGN PATENT DOCUMENTS

| | | | |
|---|---|---|---|
| CA | 1274339 | 7/1987 | |
| CA | 1278141 | 10/1987 | |
| CH | 463 778 | 10/1968 | |
| DE | 282711 | 3/1915 | |
| DE | 963 184 | 5/1957 | |
| DE | A-2111910 | 10/1971 | |
| DE | A-2429515 | 1/1975 | |
| DE | 26 50 226 | 5/1978 | |
| DE | 33 32 633 A | 4/1985 | |
| EP | 0 005 232 A | 11/1979 | |
| EP | 0 126 684 B1 | 11/1984 | |
| EP | 0 212 959 B1 | 3/1986 | |
| EP | 0 197 718 B1 | 10/1986 | |
| EP | 0 219 208 B1 | 4/1987 | |
| EP | 0 355 750 | 2/1990 | |
| EP | 393926 | 10/1990 | |
| EP | 0 393 926 | 10/1990 | |
| EP | 0 539 805 | 5/1993 | |
| EP | 0 555 750 | 6/1993 | |
| EP | 0 638 309 A1 | 2/1995 | |
| EP | 0676 201 | 10/1995 | |
| FR | 1199252 | 6/1959 | |
| FR | 7 723 M | 3/1970 | |
| FR | 2 205 333 | 5/1974 | |
| FR | 2 305 182 | 10/1976 | |
| GB | 810108 | 3/1959 | |
| GB | 838994 | 6/1960 | |
| GB | 1263044 | 2/1972 | |
| GB | 1379111 | 1/1975 | |
| GB | 1474775 | 5/1977 | |
| GB | 1545767 | * 5/1979 | |
| JP | 3-205402 | 9/1991 | |
| JP | 4-13684 | 1/1992 | |
| JP | 040 13684 A2 | 1/1992 | |
| JP | 032 05402 A2 | 9/1992 | |
| JP | 042 75223 A2 | 9/1992 | |
| JP | 4-275223 | 9/1992 | |
| JP | 042 75296 A2 | 9/1992 | |
| JP | 4-275296 | 9/1992 | |
| WO | WO 90/07502 | 7/1990 | |
| WO | 92/00281 | 1/1992 | |
| WO | WO 92/05770 | 4/1992 | |
| WO | WO 92/15286 | 9/1992 | |
| WO | WO 93/05096 | 3/1993 | |
| WO | WO 93/18748 | 9/1993 | |
| WO | WO 95/04720 | 2/1995 | |
| WO | WO 95/24379 | 9/1995 | |
| WO | WO 95/29895 | 11/1995 | |
| WO | WO 95/30409 | 11/1995 | |
| WO | WO 96/28167 | 9/1996 | |
| WO | WO 96/33268 | 10/1996 | |
| WO | WO 97/30054 | 8/1997 | |
| WO | WO 97/38977 | 10/1997 | |
| WO | WO 98/27975 | 7/1998 | A61K/31/165 |
| WO | WO 99/11622 | 3/1999 | |
| WO | WO 99/11623 | 3/1999 | |
| WO | WO 99/11624 | 3/1999 | |
| WO | WO 99/11628 | 3/1999 | |
| WO | WO 99/11644 | 3/1999 | |
| WO | WO 99/11645 | 3/1999 | |
| WO | WO 99/11649 | 3/1999 | |
| WO | WO 99/59973 | 11/1999 | |
| WO | WO 99/59975 | 11/1999 | |
| WO | WO 00/32579 | 6/2000 | |
| WO | WO 00/39070 | 7/2000 | |
| WO | WO 00/39104 | 7/2000 | |
| WO | WO 00/42040 | 7/2000 | |
| WO | WO 00/44726 | 8/2000 | |
| WO | WO 00/64878 | 11/2000 | |
| WO | WO 00/67734 | 11/2000 | |
| WO | WO 00/68206 | 11/2000 | |
| WO | WO 01/16136 | 3/2001 | |

| WO | WO 01/16137 | * | 3/2001 |
| WO | WO 01/42219 | | 6/2001 |
| WO | WO 01/91796 A2 | | 12/2001 |

OTHER PUBLICATIONS

Abstr Pap Am Chem Soc 206(2) 1993 Slama et al.
Abstract 1994:425593 1994 Zailsev et al.
Angew. Chem. 76:1, 50 1964 Baer et al.
Ann. 673:132–36 1964 Reid et al.
Ann. Chem. 688:177–88 1965 Reid et al.
Ann. N Y Acad Sci. 825:366–79 1997 Cosi et al.
Annu. Rev. Neurosci 13, 171–82 1990 Choi et al.
Anticancer Drug Des. 7:107–17 1991 Suto et al.
Anticancer Drug Design 10(6)507–14 (Sep. 1995) Griffin et al.
Anti–Cancer Drug Design 10(6):507–14 1995 R. Griffin et al.
Anticancer Research 11:881–888 1991 Sakagami et al.
Arch. Pharm. Ber. Dtsch. Pharm. Ges. 300:6, 533–39 1967 Reisch.
Beilstein Handbook of Organic Chem. Reg. No. 158523 1950.
Beilstein Handbook of Organic Chem. Reg. No. 233692 1956.
Beilstein Handbook of Organic Chem. Reg. No. 3140506 1998.
Beilstein Handbook of Organic Chem. Reg. No. 56052 1998.
Beilstein Handbook of Organic Chem. Reg. No. 332938 1998.
Beilstein Handbook of Organic Chem. Reg. No. 254129 1998.
Beilstein Handbook of Organic Chem. Reg. No. 245245 1998.
Beilstein Handbook of Organic Chem. Reg. No. 244756 1998.
Beilstein Handbook of Organic Chem. Reg. No. 222316 1998.
Beilstein Handbook of Organic Chem. Reg. No. 207532 1998.
Beilstein Handbook of Organic Chem. Reg. No. 207516 1998.
Beilstein Handbook of Organic Chem. Reg. No. 165349 1998.
Beilstein Handbook of Organic Chem. Reg. No. 161148 1998.
Beilstein Handbook of Organic Chem. Reg. No. 2213597 1999.
Beilstein Handbook of Organic Chem. Reg. No. 13823 1999.
Biochem. J. 185, 775–77 1980 Purnell et al.
Biochemical and Biophysical Research Communications 136(3), 1110–15 1986 Tanuma et al.
Biochemical and Biophysical Research Communications 195, No. 2, 558–564 1993 Jesser et al.
Biochemical and Biophysical Research Communications 195,(2), 558–64 1993 Jesser et al.
Biochemical and Biophysical Research Communications 210, No. 2, 329–337 1995 Aoki et al.
Biochemical and Biophysical Research Communications 220, 411–17 1996 Uchiumi et al.
Biochemical and Biophysical Research Communications 236, 265–69 1997 Maruta et al.
Biochemical and Biophysical Research Communications 245, 1–10 1998 Rhun et al.
Biochemical and Biophysical Research Communications 278(3) Nov. 30, 2000, 590–598 Zhang et al.
Biochemical Society Transactions vol. 8 (2), 192–193 1980 Whitby et al.
Biochemical Society Transactions 21:330–334 1993 Beckman et al.
Biochemistry 30, 5907–5912 1991 Maruta et al.
Biochemistry International 16, No. 3, 397–403 1988 Concha et al.
Biochemistry International 19, No. 6, 1395–1402 1989 Tanuma et al.
Biochemistry International 18, No. 4, 701–708 1989 Tanuma et al.
Biochemistry International 24, No. 5, 889–897 1991 Tsai et al.
Biochimica et Biophysica Acta 827, 228–234 1985 Tavassoli et al.
Biochimica et Biophysica Actas 1158, 251–56 1993 Aoki et al.
Bioorganic & Medicinal Chem. Letters 11 (2001) 1687–1690 Li et al.
Br. J. Pharm. 117:619–32 1996 Southan et al.
Brain Res. 710:169–77 1996 Wallis et al.
Brain Res. 729:264–69 1996 Cosi et al.
Brain Research 809:58–67 1998 Cosi et al.
Brain Research 842 (1999) 109–118 Sauer et al.
Brain 122,247–253 1999 Love et al.
Brit. J. Pharm. 122:493–503 1997 Cuzzocrea.
Bull. Chem. Soc. Jpn. 61(6):2238–40 1988 Sato et al.
Bull. Soc. Chim. Fr. 233 1962 Granger et al.
C. R. Acad. Sci. 275:17, 961–64 1972 Michailidis et al.
Can. J. Chem. vol. 49, 2797–2802 1971 Horning.
Cell 94, 325–337 1998 Kuida et al.
Cell 94, 339–352 1998 Hakem et al.
Cell Biology and Toxicology 9, No. 2, 165–175 1993 Clayson et al.
Cerebrovascular Disease 319–25 1997 Dawson et al.
Chem Abstracts 52:17 (14606h) (Sep. 10, 1958) Ochiai et al.
Chem Abstracts 55:6 (5491ce) (Mar. 20, 1961) Ochiai et al.
Chem Abstracts 58:4 (3425d) (Feb. 18, 1963) Hayashi et al.
Chem Abstracts vol. 126,No. 17,229493f (Apr. 28, 1997) Angeliki.
Chem. Abstracts 64:695e 1966 Ried et al.
Chem. Ber. 46, pp. 2087, 2089 1913 Kardos.
Chemical Abstract 54:22648a 1995 Nikitskaya et al.
Chemical Abstract vol. 51:1960 1957 Taylor et al.
Chemical Abstract vol. 52:5846a 1958 Schmidt–Nickels.
Chemical Abstract vol. 52:6285 1958 Ohta.
Chemical Abstract vol. 52:4646 1958 Gilman et al.
Chemical Abstract vol. 52:5846b 1958 Gateff et al.
Chemical Abstract vol. 54:22647 1960 Campbell.
Chemical Abstract vol. 55:12868a 1961.
Chemical Abstract vol. 55:12868b 1961.
Chemical Abstract vol. 55:12868c 1961.
Chemical Abstract vol. 58:7884 1963 Sieglitz.
Chemical Abstract vol. 59:10037b 1963 Dokunikhin et al.
Chemical Abstract vol. 59:10037c 1963 Hazard et al.
Chemical Abstract vol. 61:15194 1964 Tsuboi.
Chemical Abstract vol. 61:13305h 1964 Quelet.
Chemical Abstract vol. 61:9493g 1964 Dokunikhin et al.
Chemical Abstract vol. 61:9494a 1964 Dokunikhin et al.
Chemical Abstract vol. 61:9493f 1964 Bodea et al.

Chemical Abstract vol. 61:13305g 1964 Badger et al.
Chemical Abstract vol. 63:7006 1965 Perrin.
Chemical Abstract vol. 62:5259 1965 Lakeside Lab., Inc.
Chemical Abstract vol. 62:9129e 1965 Kuehn.
Chemical Abstract vol. 63:4256 1965 Keene et al.
Chemical Abstract vol. 62:9129g 1965 Klosa.
Chemical Abstract vol. 65:15320a 1966 Kametani.
Chemical Abstract vol. 64:3526h 1966 Crossland.
Chemical Abstract vol. 65:15319h 1966 Humber et al.
Chemical Abstract vol. 69:87767 1968 Hofer.
Chemical Abstract vol. 68:59420 1968 Chandler et al.
Chemical Abstract vol. 70:3629 1969 Weis.
Chemical Abstract vol. 70:67988 1969 Resplandy et al.
Chemical Abstract vol. 70:115926 1969 Hofer.
Chemical Abstract vol. 70:4079 1969 Coyne et al.
Chemical Abstract vol. 73:35200 1970 Pan et al.
Chemical Abstract, vol. 72:121337 1970 Pan et al.
Chemical Abstract vol. 74:111797 1971 Mavoungou–Gomes.
Chemical Abstract vol. 75:98422 1971 Campbell.
Chemical Abstract 74:110112y (p. 252 May 10, 1971) Damas.
Chemical Abstract vol. 77:61927 1972 Zinchenko.
Chemical Abstract vol. 76:14566 1972 Rodway.
Chemical Abstract vol. 76:85774 1972 Mavoungou–Gomes.
Chemical Abstract vol. 78:123624 1973 Swenton et al.
Chemical Abstract vol. 78:68700 1973 Roehm et al.
Chemical Abstract vol. 78:58193 1973 Mondon et al.
Chemical Abstract vol. 78:84227 1973 Kraatz et al.
Chemical Abstract vol. 78:29384 1973 Forrester et al.
Chemical Abstract vol. 78:29593 1973 Cerbai et al.
Chemical Abstract vol. 81:37489 1974 Cerbai et al.
Chemical Abstract vol. 81:37417 1974 Baddar.
Chemical Abstract vol. 82:171011 1975 Rodway.
Chemical Abstract vol. 82:170471 1975 Mavoungou–Gomes.
Chemical Abstract vol. 83:27978 1975 Baddar.
Chemical Abstract vol. 84:42754 1976 Zaitsev.
Chemical Abstract vol. 84:3986 1976 Zaitsev.
Chemical Abstract vol. 85:182 1976 Tullar et al.
Chemical Abstract vol. 84:16943 1976 Minatoya et al.
Chemical Abstract vol. 85:77216 1976 Ege et al.
Chemical Abstract vol. 84:4857 1976 Cookson.
Chemical Abstract 85(1976)159898a.
Chemical Abstract vol. 86:171282 1977 Humber.
Chemical Abstract vol. 87:152015 1977 Houlihan.
Chemical Abstract vol. 87:5778 1977 Fomenko et al.
Chemical Abstract vol. 82:30602 1978 Minatoya et al.
Chemical Abstract vol. 90:6486t 1979 Takahashi.
Chemical Abstract vol. 91:39035 1979 Migachev.
Chemical Abstract vol. 90:38734 1979 Mavoungou–Gomes.
Chemical Abstract vol. 92:181104e 1980 Ryabukhina et al.
Chemical Abstract vol. 92:146482 19880 Rokach.
Chemical Abstract vol. 92:41620 1980 Migachev et al.
Chemical Abstract vol. 92:41511 1980 Migachev et al.
Chemical Abstract vol. 93:26178 1980 Gomes.
Chemical Abstract vol. 92:198336 1980 Cabares.
Chemical Abstract 92:22393 1980 Simmonds.
Chemical Abstract vol. 95:80661 1981 Narasimhan et al.
Chemical Abstract vol. 95(9):80666 1981 Migachev et al.
Chemical Abstract vol. 95:80688 1981 Migachev et al.
Chemical Abstract vol. 95:42867 1981 Migachev et al.
Chemical Abstract vol. 95:42866 1981 Migachev et al.
Chemical Abstract vol. 95:187120 1981 Migachev et al.
Chemical Abstract vol. 95:168911 1981 Houlihan.
Chemical Abstract vol. 96:6539m, p. 592 1982 Singh et al.
Chemical Abstract vol. 96:68519 1982 Leardini et al.
Chemical Abstract vol. 97:38635 1982 Krepelka.
Chemical Abstract vol. 97:126680 1982 Grimshaw et al.
Chemical Abstract vol. 100:103453 1984 Prostakov et al.
Chemical Abstract vol. 100:191713 1984 Orlic–Nuber et al.
Chemical Abstract vol. 100:139054 1984 Oleinik.
Chemical Abstract vol. 102:203854 1985 Migachev et al.
Chemical Abstract vol. 105:60505 1986 Andrievskii et al.
Chemical Abstract vol. 106 (67553) 1987 Pellefier.
Chemical Abstract vol. 107:23262 1987 Cabares.
Chemical Abstract vol. 107:39655v 1987 Bondarenko et al.
Chemical Abstract vol. 108:21627 1988 Duval.
Chemical Abstract vol. 110:230971 1989 Val'kova et al.
Chemical Abstract vol. 113:190649 1990 Val'kova et al.
Chemical Abstract vol. 112:44716 1990 Korol'kova et al.
Chemical Abstract vol. 112:128235 1990 Korol'kova et al.
Chemical Abstract vol. 112:216749 1990 Benson et al.
Chemical Abstract vol. 114: 143456 1991 Walser.
Chemical Abstract vol. 115: (232107) 1991 Nagao.
Chemical Abstract vol. 115:70731f 1991 Donshikh et al.
Chemical Abstract vol. 115:158338 1991 Buckman et al.
Chemical Abstract vol. 114:42543 1991 Andrievskii et al.
Chemical Abstract vol. 119:72127 1993 Zaitsev et al.
Chemical Abstract vol. 118:191567 1993 Dow.
Chemical Abstract vol. 118:80722 1993 Dininno et al.
Chemical Abstract vol. 118:101709 1993 Dininno et al.
Chemical Abstract vol. 120:134231 1994 Rocca et al.
Chemical Abstract vol. 121:220651v 1994 Pawlowska et al.
Chemical Abstract vol. 121:172572 1994 Liu et al.
Chemical Abstract vol. 120:95793 1994 Kyota et al.
Chemical Abstract vol. 121:57315 1994 Dow et al.
Chemical Abstract vol. 120:148508p 1994 Barros et al.
Chemical Abstract, vol. 123:505 1995 Weltin et al.
Chemical Abstract vol. 122:10865 1995 Lamba et al.
Chemical Abstract vol. 122:170499 1995 Korol'kova et al.
Chemical Abstract vol. 123:256711 1995 Kalindjian et al.
Chemical Abstract vol. 122:170250 1995 Gorio et al.
Chemical Abstract vol. 122:187249 1995 Dininno et al.
Chemical Abstract 122:316902 1995 Desilets et al.
Chemical Abstract 122:316901 1995 Desilets et al.
Chemical Abstract 122:187526 1995 Langlois et al.
Chemical Abstract vol. 125:87882 1996 Yamaguchi et al.
Chemical Abstract vol. 124:331706 1996 Silverman et al.
Chemical Abstract vol. 124:131261 1996 Richter.
Chemical Abstract vol. 126:115554 1996 Malhotra et al.
Chemical Abstract vol. 125:246943 1996 Korol'kova et al.
Chemical Abstract vol. 125:277462 1996 Ge et al.
Chemical Abstract 124:202047 1996 Fernandez et al.
Chemical Abstract vol. 128:36109 1997 Sakai et al.
Chemical Abstract vol. 127:234258 1997 Reddy et al.
Chemical Abstract vol. 127:81282 1997 Marek et al.
Chemical Abstract vol. 128:34752 1997 Jones et al.
Chemical Abstract vol. 127:80243 1997 Banister et al.
Chemical Abstract abstract No. 17462 1998 Yoshida et al.
Chemical Abstract vol. 129:104224 1998 West.
Chemical Abstract vol. 128:138099 1998 Weltin et al.
Chemical Abstract vol. 130:24816 1998 Park et al.
Chemical Abstract vol. 128:75320 1998 Jones et al.
Chemical Abstract vol. 128:165850 1998 Cookson et al.
Chemical Abstract vol. 129:54301 1998 Albright et al.
Chemical Abstract No. 816103 1998 Albright et al.
Chemical Abstracts vol. 52 (21) 18420d 1958 Tanida.

Chemical Abstracts vol. 62, No. 5, 5271c Mar. 1965.
Chemical Abstracts vol. 76 (25) 153704b 1972 Pozharskii et al.
Chemical Abstracts vol. 88 (7) 49887 1978 Szadowski.
Chemical Abstracts 88, No. 13, 505 (88:89502c) 1978 Dokunikhin et al.
Chemical Abstracts 94, No. 23, 637 (192098y) 1981 Migachev.
Chemical Abstracts Registry No. 17 1399–15–8 1998.
Chemical Abstracts Registry No. 14223 8–47–9 1998.
Chemical Abstracts 85:159898a 85, No. 21, 531 1974 Upadysheva et al.
Chem. Lett. 39–42, 1990 Chiba et al.
Chemical and Pharmaceutical Bulletin vol. 26, No. 12, pp. 3682–3694 1978 Hamada et al.
Chemische Berichte vol. 102, 1161–1176 1969 Kauffmann et al.
Cir. Res. 83:85–94 (1998) Zingarelli et al.
Emerging Drugs—Ashley Pub. (1999) 4:209–221 Zhang et al.
Eur. J. Pharm. 204, 339–40 1991 Nowicki et al.
European Journal of Pharmacology 351(1998) p. 377 Endres et al.
Gastroenterology, 1999; 116: p. 335 Zingarelli et al.
Gazz. Chim. Ital. 91:1345–51 1962 Di Maio et al.
Gazz. Chim. Ital. 91:1124–32 1962 Di Maio et al.
Gazz. Chim. Ital. 94:5, 590–94 1964 Di Maio et al.
Hawleys Chemical Condense Dictionary Sax (Ed) 11th Ed, 1987 p898 Hawley's.
Heterocycles 22:2, 237–40 1984 Naito et al.
Heterocycles 2000, 52(1) 325–332 Zhao et al.
Heterocycles 1990, 31(3) 419–422 Friary et al.
Idrugs 2001 4(7):804–812 Li et al.
Int. J. Immunopharmac 17, No. 4, 265–271 1995 Weltin et al.
Int. J. Radiat. Biol. vol. 72 No. 6, pp. 685–692 1997 Weltin et al.
Int. J. Radiat. Biol. Relat. Stud. Phys. Chem. Med. vol. 48 No. 5, pp. 675–690 1985 Harris.
Intl. J. Oncol 8:239–52 1996 Bauer et al.
IPER for PCT/US98/18189.
IS&T's Tenth Int'l Congress on Advances in Non–Impact Printing Technologies 246–248 1994 Richter et al.
Itsu Kenkusho Nempo 16:15–23 1971 Ochiai et al.
J Cerebral Flood Flow Metabol. 17(11): 1143–51 1997 Endres et al.
J Chem. Soc. 11:1293–97 1978 Davies et al.
J. Am. Chem. Soc. 78:5104–8 1956 Taylor et al.
J. Biol. Chem 270:19, 11176–80 1995 Heller et al.
J. Biol. Chem. 246(20), 6362–64 1972 Miwa et al.
J. Biol. Chem. 261(32), 14902–11 1986 Hatakeyama et al.
J. Biol. Chem. 262(36), 17641–50 1987 Ikejima et al.
J. Biol. Chem. 263(23), 11037–40 1988 Ikejima et al.
J. Biol. Chem. 267(20), 14436–42 1992 Tsai et al.
J. Biol. Chem. 267:3, 1569–75 1992 Banasik et al.
J. Biol. Chem. 272:9030–36 1997 Szabó et al.
J. Chem Soc. 12:2231–2241 1971 Barton.
J. Chem. Res., Synop. 8:302 1995 Mueller et al.
J. Chem. Res., Synop. 2:126 1996 Mueller et al.
J. Chem. Soc. pp. 1979–1984 1929 Blount et al.
J. Chem. Soc. 1624–28 1958 Johnson.
J. Chem. Soc. 4295–98 1962 Brown et al.
J. Chem. Soc. 1:14, 1747–51 1974 Ninomiya et al.
J. Chem. Soc. 1:7, 763–70 1974 Bailey et al.

J. Chem. Soc. 812 1956 McConnell et al.
J. Exp. Med. vol. 186, No. 7, Oct. 6, 1997, 1041–9 Szabo.
J. Het. Chem. vol. 7, pp. 597–605 1970 Pan et al.
J. Heterocycl. Chem. 20:5, 1407–9 1983 Rougeot et al.
J. Immuno. 153:3319–25 1994 Hughes et al.
J. Med. Chem. 38, 389–393 1995 Slama et al.
J. Med. Chem. 38, 4332–4336 1995 Slama et al.
J. Med. Pharm. Chem. 3; 1961; 157, 159 1961 Gootjes et al.
J. Mol. Cell Cardiol 31, 297–303 (1999) Grupp et al.
J. Neurochem 65:3, 1411–14 1995 Zhang et al.
J. Neurosci 13:6, 2651–61 1993 Dawson et al.
J. Neurosci. 16:8, 2479–87 1996 Dawson et al.
J. Neuroscience Res. 47: 372–383 1997 Ceruti et al.
J. of Biological Chemistry 261(2), 965–69 1986 Tanuma et al.
J. Org Chem. 29:3, 681–85 1964 Masamune et al.
J. Org Chem. 47, 2043–2047 1982 Taylor et al.
J. Org. Chem. vol. 23, pp. 1071–1072 Jul. 1958 Robinson et al.
J. Org. Chem. 29:11, 3180–85 1964 Baer et al.
J. Org. Chem. 43:11, 2190–96 1978 Eisch et al.
J. Phys. Org. Chem 10; 7; 1997; 499–513 Arnett et al.
JACS 71:937–8 (Mar. 1949) Wilson et al.
JACS 76:4396–8 (Sep. 5, 1954) Wright.
Japanese J. Pharm. 75, Supp. I:102 1997 Szabó et al.
Japanese J. Pharm. 75, Supp. I:15 1997 Salzman et al.
JCS pp. 4067–4075 1952 Peak et al.
JCS, pp1294–304, 1956, Albert et al.
JCS pp 2384–96 1959 Albert et al.
Journal of Cellular Biochemistry 29:361–372 1985 Bolander, Jr.
Journal of Cerebral Blood Flow and Metabolism 17 No 11, 1137–1142 1997 Takahashi, et al.
Journal of Heterocyclic Chemistry vol. 3, pp. 466–469 Dec., 1966 Aparajithan.
Journal of Heterocyclic Chemistry vol. 15, pp. 1513–1514 1978 Nuvole et al.
Journal of Medicinal Chemistry vol. 20 (3) 449–452 1977 Diana et al.
Journal of Medicinal Chemistry 35(5)823–832 1992 Ocain.
Journal of Medicinal Chemistry 1979, vol. 22, No. 7,845–849 Lazar et al.
Journal of Neurochemistry 70, No. 2, 501–508, 1998 Cookson et al.
Journal of Organic Chemistry vol. 11, No. 3, 239–246, 1946 Bergstrom et al.
Journal of Organic Chemistry 53(20):4650–3 1988 D. Dumas.
Journal of the Chemical Society pp. 1799–1803 1972 Singh et al.
Journal of the Chemical Society vol. 9, 944–950 1976 Loewenthal et al.
Justus Liebigs Ann. Chem. 388, p. 212 1912 Ullmann et al.
Life Sciences 63 (23) 2133 (1998) Szabo.
Med Chem. Res. 6:2, 81–101 1996 Castan et al.
Molec. Cell. Biochem. 138:185–97 1994 Banasik et al.
Mutation Research 281, 67–74 1989 Gonzalez et al.
Mutation Research 350, 25–34 1996 Wachsman.
Nature Medicine JHU 1997 Eliasson et al.
Neuron 1, 623–634 1988 Choi.
NeuroReport 5:3, 245–48 1993 Wallis et al.
Neurological Research Aug. 1995, vol. 17, (285–288) Zhang et al.

Nucleic Acids Research 29(3) 841–849 2001 Simbulan–Rosenthal et al.
Oncol. Res. 6:9, 399–403 1994 Weltin et al.
Pharm. Bull. 5:289–91 1957 Ochiai et al.
Phosphorus Sulfur vol. 14, No. 1, pp. 131–138 1983 Becher et al.
Proc. Natl. Acad. Sci. USA 88:6368–71 1991 Dawson et al.
Proc. Natl. Acad Sci. USA, 93:1753–58, 1996, Szabó et al.
Proc. Natl. Acad Sci. USA, 94:679–83, 1997, Thiemermann et al.
Proc. Natl. Acad. Sci. USA, 96:5774–5779, (May 1999), Mandie et al.
Radiat. Res. 101:29–46 1985 Oleinik.
Ric. Sci., 38:3 231–33 1968 Di Maio et al.
Rocz. Chem. 41:1,89–101 1967 Schoen et al.
Science 223:589–91 1984 Milam et al.
Science 263:687–89 1994 Zhang et al.
Science 265:1883–1885 1994 Huang et al.
Science 282, 1484–1487 1998 Smith et al.
Shock 5(4):258–64 1996 Zingarelli et al.
Shock 13(1) p 60 (2000) Yang et al.
Shock 9(5) p 341 (1998) Szabo.
Soc. for Neuro., 28$^{th}$ Ann Meeting 1998, L.A., CA#480.14 Zhang et al.
Soc. for Neuro., 28$^{th}$ Ann Meeting 1998, L.A., CA#480.16 Lautar et al.
Soc. for Neuro., 28$^{th}$ Ann Meeting 1998, L.A. CA#433.9 Williams et al.
Spin Label Analogue of ATP 246, No. 20, 6362–6364 1971 Miwa et al.
Switzerland Patent 601 246 1978.
Terato., Carcino., and Muta. 16:219–27 1996 Cristovao et al.
Tetrahedron supp. 8, part 1, pp. 305–312 1966 Tamayo et al.
Tetrahedron 1990, 46(4) 1253–1262 Duval et al.
Tetrahedron Letters 32, No. 35, 4525–4528 1991 Chida et al.
Tetrahedron Letters 36:33, 5983–86 1995 White et al.
Tetrahedron Letters 1992, 33(45) 6775–6778 Lopes.
Tetrahedron Letters 52:9, 3117–34 1996 White et al.
The Journal of Biological Chemistry 242, No. 22, 5301–5307 1967 Futai et al.
The Journal of Biological Chemistry vol. 257, No. 21, 12872–12877 1982 Wielckens et al.
The Journal of Biological Chemistry 259, No. 2, 986–995 1984 Oka et al.
The Journal of Biological Chemistry 261, No. 2, pp. 965–969 1986 Tanuma et al.
The Journal of Biological Chemistry 263, No. 23, 11037–11040 1988 Ikejima et al.
The Journal of Biological Chemistry 272, No. 18, 11895–11901 1997 Lin et al.
TiPS 11, 379–387 1990 Meldrum et al.
TIPS in press 1998 Pieper et al.
TIPS Apr. 1999 (vol. 200 Pieper et al.
Trends Neurosci. 20:3, 132–139 1997 Iadecola.
Vertex Pharmaceuticals Inc. PR Newswire 1998.
Zhang et al, "Poly (ADP–Ribose) Polymerase Inhibition by Genetic and Pharmacological Means", Cell Death: the Role of PARP, Chapter 13, pp. 279–304, 2000.
LaPlaca et al, "Pharmacologic Inhibition of Poly (ADP–Ribose) Polymerase is Neuroprotective Following Traumatic Brain Injury in Rats", Journal of Neurotrauma, vol. 18, No. 4, 2001, pp. 369–376.
Dokunichin, Beilstein Handbook of Organic Chem., Reg. No. 618403, 1988.
Dokunichin, Beilstein Handbook of Organic Chem., Reg. No. 827161, 1988.
Dokunichin, Beilstein Handbook of Organic Chem., Reg. No. 821484, 1988.
Dokunichin, Beilstein Handbook of Organic Chem., Reg. No. 619108, 1988.
Dokunichin, Beilstein Handbook of Organic Chem., Reg. No. 657772, 1988.
Dokunichin, Beilstein Handbook of Organic Chem., Reg. No. 653888, 1988.
Oleinik, Beilstein Handbook of Organic Chem., Reg. No. 4483194, 1991.
Oleinik, Beilstein Handbook of Organic Chem., Reg. No. 4494786, 1991.
Sielitz, Beilstein Handbook of Organic Chem., Reg. No. 807993, 1988.
Dokunichin, Beilstein Handbook of Organic Chem., Reg. No. 746893, 1988.
Gomes, Beilstein Handbook of Organic Chem., Reg. No. 656117, 1988.
Rokach, Beilstein Handbook of Organic Chem., Reg. No. 1571164, 1988.
Humber et al., Beilstein Handbook of Organic Chem., Reg. No. 1541605, 1988.
Mavoungou Gomes, Beilstein Handbook of Organic Chem., Reg. No. 751834, 1988.
Mavoungou Gomes, Beilstein Handbook of Organic Chem., Reg. No. 670954, 1988.
Dokunichin, Beilstein Handbook of Organic Chem., Reg. No. 649696, 1988.
Dokunichin, Beilstein Handbook of Organic Chem., Reg. No. 660681, 1988.
Dokunichin, Beilstein Handbook of Organic Chem., Reg. No. 530731, 1988.
Purnell et al., "Novel Inhibitors of Poly(ADP–Ribose) Synthetase", Biochem. J. (1980), vol. 185, 775–777.
Weltin et al., "Effect of 6(5H)–phenanthridinone, a poly (ADP–ribose)polymerase inhibitor, and ionizing radiation on the growth of cultured lymphoma cells".
Fernandez et al., Chemical Abstract search result, 124:202047 (1996).
Desilets et al., Chemical Abstract search result, 122:316902 (1995).
Desilets et al., Chemical Abstract search result, 122:316901 (1995).
Langloise et al., Chemical Abstract search result, 122: 187526 (1995).
Simmonds, Chemical Abstract search result, 92:22393 (1980).
Ullmann et al., Justus Liebigs Ann. Chem. (Chemical Abstract search result), 388, p. 212 (1912).
Kardos, Chem. Ber. (Chemical Abstract search result), 46, pp. 2087, 2089 (1913).
Nikitskaya et al., Chemical Abstract, 54:22648a (no year reported).
Desilets et al., "Design and Synthesis of Near–Infrared Absorbing Pigments", Can. J. Chem., 73, 319–35 (1995). (Part I and Part II).
Langlois et al., "Synthesis of Quinazoline–2, 4–dione and Naphthalimide Derivatives as New 5–HT3 Receptor Antagonists", Eur. J. Med. Chem., 29, 925–40 (1994).

Mao et al., "The inhibition of nitric oxide–activated poly (ADP–ribose) synthetase attenuates transsynaptic alteration of spinal cord dorsal horn neurons and neuropathic pain in the rat", Pain vol. 72, pp. 355–366 (1997).

Ruf et al., "Structure of the catalytic fragment of poly (ADP–ribose) polymerase from chicken", Proc. Natl. Acad. Sci. USA vol. 93, pp. 7481–7485 (Jul. 1996).

Vaziri et al., "ATM–dependent telomere loss in aging human dipoloid fibroblasts and DNA damage lead to the post–translational activation of p53 protein involving poly (ADP–ribose) polymerase", The EMBO Journal vol. 16 No. 19, pp. 6018–6033 (1997).

R. J. Griffin et al., Abstract of "The role of poly(ADP–ribose) polymerase as resistance–modifying agents in cancer therapy", Biochimie vol. 77 No. 6, pp. 408–422 (1995).

A. L. Harris, Abstract of "DNA repair: relationship to drug and radiation resistance, metastasis and growth factors", Int. J. Radiat. Biol. Relat. Stud. Phys. Chem. Med. vol. 48 No. 5, pp. 675–690 (1985).

Tim T. Lam, "The effect of 3–aminobenzamide, an inhibitor of poly–ADP–ribose polymerase, on ischemia/reperfusion damage in rat retina", Res. Comm. Mol. Pathol. Pharmacol. vol. 95 No. 3, pp. 241–252 (Mar. 1997).

Jianren Mao et al., "The inhibition of nitric oxide–activated poly (ADP–ribose) synthetase attenuates transsynaptic alteration of spinal cord dorsal horn neurons and neuropathic pain in the rat", Pain vol. 72, pp. 355–366 (1997).

G. P. Paaphorst & E.I. Azzam, Full citation of "Poly–ADP–ribose synthetase inhibitors increase radiation and thermal sensitivity but do not affect thermotolerance", Radiat. Res. vol. 116, No. 3, pp. 442–452 (1988).

Armin Ruf et al., "Structure of the catalytic fragment of poly (ADP–ribose) polymerase from chicken", Proc. Natl. Acad. Sci. USA vol. 93, pp. 7481–7485 (Jul. 1996).

Geoffrey N. Sklar et al., "Combined antitumor effect of suramin plus irradiation in human prostate cancer cells: the role of apoptosis", J. Urol. vol. 150, pp. 1526–1532 (Nov. 1993).

Léon Van Gool et al., "Overexpression of human poly (ADP–ribose) polymerase in transfected hamster cells leads to increased poly(ADP–ribosyl)ation and cellular sensitization to $\gamma$ irradiation", Eur. J. Biochem. vol. 244, pp. 15–20 (1997).

Homayoun Vaziri et al., "ATM–dependent telomere loss in aging human dipoloid fibroblasts and DNA damage lead to the post–translational activation of p53 protein involving poly(ADP–ribose) polymerase", The EMBO Journal vol. 16 No. 19, pp. 6018–6033 (1997).

\* cited by examiner

COMPOUNDS, METHODS AND PHARMACEUTICAL COMPOSITIONS FOR TREATING NEURAL OR CARDIOVASCULAR TISSUE DAMAGE

This application is a continuation-in-part application of U.S. patent application Ser. No. 09/047,502, filed Mar. 25, 1998, now U.S. Pat. No. 6,306,889 which is a continuation-in-part of of U.S. patent application Ser. No. 08/922,548, filed Sep. 3, 1997, now U.S. Pat. No. 6,346,536 the contents of which are incorporated herein in their entirety.

BACKGROUND OF THE INVENTION

1. Field of the Invention

The present invention relates to inhibitors of the nucleic enzyme poly(adenosine 5'-diphospho-ribose)polymerase ["poly(ADP-ribose)polymerase" or "PARP", which is also sometimes called "PARS" for poly(ADP-ribose)synthetase]. More particularly, the invention relates to the use of PARP inhibitors to prevent and/or treat tissue damage resulting from cell damage or death due to necrosis or apoptosis; neural tissue damage resulting from ischemia and reperfusion injury; neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

2. Description of the Prior Art

Poly(ADP-ribose)polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been fully established, this enzyme is thought to play a role in enhancing DNA repair.

During major cellular stresses, however, the extensive activation of PARP can rapidly lead to cell damage or death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose)Synthetase in Neurotoxicity", *Science*, 263:687–89 (1994)); and in hippocampal slices (Wallis et al., "Neuroprotection Against Nitric Oxide Injury with Inhibitors of ADP-Ribosylation", *NeuroReport*, 5:3, 245–48 (1993)). The potential role of PARP inhibitors in treating neurodegenerative diseases and head trauma has thus been known. Research, however, continues to pinpoint the exact mechanisms of their salutary effect in cerebral ischemia, (Endres et al., "Ischemic Brain Injury is Mediated by the Activation of Poly(ADP-Ribose)Polymerase", *J. Cereb. Blood Flow Metabol.*, 17:1143–51 (1997)) and in traumatic brain injury (Wallis et al., "Traumatic Neuroprotection with Inhibitors of Nitric Oxide and ADP-Ribosylation, *Brain Res.*, 710:169–77 (1996)).

It has been demonstrated that single injections of PARP inhibitors have reduced the infarct size caused by ischemia and reperfusion of the heart or skeletal muscle in rabbits. In these studies, a single injection of the PARP inhibitor, 3-amino-benzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose)Synthetase Reduces Ischemia-Reperfusion Injury in the Heart and Skeletal Muscle", *Proc. Natl. Acad. Sci. USA*, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage", *J. Neurochem.*, 65:3, 1411–14 (1995). Other studies have continued to explore the role of PARP activation in cerebellar granule cells in vitro and in MPTP neurotoxicity. Cosi et al., "Poly(ADP-Ribose)Polymerase (PARP) Revisited. A New Role for an old Enzyme: PARP Involvement in Neurodegeneration and PARP Inhibitors as Possible Neuroprotective Agents", *Ann. N.Y. Acad. Sci.*, 825:366–79 (1997); and Cosi et al., "Poly(ADP-Ribose) Polymerase Inhibitors Protect Against MPTP-induced Depletions of Striatal Dopamine and Cortical Noradrenaline in C57B1/6 Mice", *Brain Res.*, 729:264–69 (1996).

Neural damage following stroke and other neurodegenerative processes is thought to result from a massive release of the excitatory neurotransmitter glutamate, which acts upon the N-methyl-D-aspartate (NMDA) receptors and other subtype receptors. Glutamate serves as the predominate excitatory neurotransmitter in the central nervous system (CNS). Neurons release glutamate in great quantities when they are deprived of oxygen, as may occur during an ischemic brain insult such as a stroke or heart attack. This excess release of glutamate in turn causes over-stimulation (excitotoxicity) of N-methyl-D-aspartate (NMDA), AMPA, Kainate and MGR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Recent studies have also advanced a glutamatergic basis for compulsive disorders, particularly drug dependence. Evidence includes findings in many animal species, as well as, in cerebral cortical cultures treated with glutamate or NMDA, that glutamate receptor antagonists block neural damage following vascular stroke. Dawson et al., "Protection of the Brain from Ischemia", *Cerebrovascular Disease*, 319–25 (H. Hunt Batjer ed., 1997). Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is no known effective treatment for glutamate abnormalities.

The stimulation of NMDA receptors, in turn, activates the enzyme neuronal nitric oxide synthase (NNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate Neurotoxicity in Primary Cortical Cultures", *Proc. Natl. Acad. Sci. USA*, 88:6368–71 (1991); and Dawson et al., "Mechanisms of Nitric Oxide-mediated Neurotoxicity in Primary Brain Cultures", *J. Neurosci.*, 13:6, 2651–61 (1993). Protection against NMDA neurotoxicity can also occur in cortical cultures from mice with targeted disruption of NNOS. See Dawson et al., "Resistance to Neurotoxicity in Cortical Cultures from Neuronal Nitric Oxide Synthase-Deficient Mice", *J. Neurosci.*, 16:8, 2479–87 (1996).

It is known that neural damage following vascular stroke is markedly diminished in animals treated with NOS inhibitors or in mice with NNOS gene disruption. Iadecola, "Bright and Dark Sides of Nitric Oxide in Ischemic Brain Injury", *Trends Neurosci.*, 20:3, 132–39 (1997); and Huang et al., "Effects of Cerebral Ischemia in Mice Deficient in Neuronal Nitric oxide Synthase", *Science*, 265:1883–85 (1994). See also, Beckman et al., "Pathological Implications of Nitric Oxide, Superoxide and Peroxynitrite Formation", *Biochem. Soc. Trans.*, 21:330–34 (1993). Either NO or peroxynitrite can cause DNA damage, which activates PARP. Further support for this is provided in Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", *Proc. Natl. Acad. Sci. USA*, 93:1753–58 (1996).

Zhang et al., U.S. Pat. No. 5,587,384 issued Dec. 24, 1996, discusses the use of certain PARP inhibitors, such as benzamide and 1,5-dihydroxy-isoquinoline, to prevent NMDA-mediated neurotoxicity and, thus, treat stroke, Alzheimer's disease, Parkinson's disease and Huntington's disease. However, it is has now been discovered that Zhang et al. may have been in error in classifying neurotoxicity as NMDA-mediated neurotoxicity. Rather, it may have been more appropriate to classify the in vivo neurotoxicity present as glutamate neurotoxicity. See Zhang et al. "Nitric Oxide Activation of Poly(ADP-Ribose)Synthetase in Neurotoxicity", *Science*, 263:687–89 (1994). See also, Cosi et al., Poly(ADP-Ribose)Polymerase Inhibitors Protect Against MPTP-induced Depletions of Striatal Dopamine and Cortical Noradrenaline in C57B1/6 Mice", *Brain Res.*, 729:264–69 (1996).

It is also known that PARP inhibitors affect DNA repair generally. Cristovao et al., "Effect of a Poly(ADP-Ribose) Polymerase Inhibitor on DNA Breakage and Cytotoxicity Induced by Hydrogen Peroxide and γ-Radiation," *Terato., Carcino., and Muta.*, 16:219–27 (1996), discusses the effect of hydrogen peroxide and γ-radiation on DNA strand breaks in the presence of and in the absence of 3-aminobenzamide, a potent inhibitor of PARP. Cristovao et al. observed a PARP-dependent recovery of DNA strand breaks in leukocytes treated with hydrogen peroxide.

PARP inhibitors have been reported to be effective in radiosensitizing hypoxic tumor cells and effective in preventing tumor cells from recovering from potentially lethal damage of DNA after radiation therapy, presumably by their ability to prevent DNA repair. See U.S. Pat. Nos. 5,032,617; 5,215,738; and 5,041,653.

Evidence also exists that PARP inhibitors are useful for treating inflammatory bowel disorders. Salzman et al., "Role of Peroxynitrite and Poly(ADP-Ribose)Synthase Activation Experimental Colitis," *Japanese J. Pharm.*, 75, Supp. I:15 (1997), discusses the ability of PARP inhibitors to prevent or treat colitis. Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.*, 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", *J. Biol. Chem.*, 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," *Japanese J. Pharm.*, 75, Supp. I:102 (1997), discusses the ability of PARP inhibitors to prevent or treat collagen-induced arthritis. See also Szabo et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite," *Proc. Natl. Acad. Sci. USA*, 93:1753–58 (March 1996); Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone ($INH_2BP$)", *Intl. J. Oncol.*, 8:239–52 (1996); and Hughes et al., "Induction of T Helper Cell Hyporesponsiveness in an Experimental Model of Autoimmunity by Using Nonmitogenic Anti-CD3 Monoclonal Antibody", *J. Immuno.*, 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," *J. Biol. Chem.*, 270:19, 11176–80 (May 1995), discusses the tendency of PARP to deplete cellular NAD+ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Further still, PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," *Shock*, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose)synthetase.- See also, Cuzzocrea, "Role of Peroxynitrite and Activation of Poly(ADP-Ribose)Synthetase in the Vascular Failure Induced by Zymosan-activated Plasma," *Brit. J. Pharm.*, 122:493–503 (1997).

Yet another known use for PARP inhibitors is treating cancer. Suto et al., "Dihydroisoquinolinones: The Design and Synthesis of a New Series of Potent Inhibitors of Poly(ADP-Ribose)Polymerase", *Anticancer Drug Des.*, 7:107–17 (1991), discloses processes for synthesizing a number of different PARP inhibitors. In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly (ADP-ribose)Polymerase, on Cultured Tumor Cells", *Oncol. Res.*, 6:9, 399–403 (1994), discusses the inhibition of PARP activity, reduced proliferation of tumor cells, and a marked synergistic effect when tumor cells are co-treated with an alkylating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. See Mao et al., *Pain*, 72:355–366 (1997).

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related macular degeneration, immune senescence, AIDS, and other immune senescence diseases; and to alter gene expression of senescent cells. See WO 98/27975.

Large numbers of known PARP inhibitors have been described in Banasik et al., "Specific Inhibitors of Poly (ADP-Ribose)Synthetase and Mono(ADP-Ribosyl)-Transferase", *J. Biol. Chem.*, 267:3, 1569–75 (1992), and in Banasik et al., "Inhibitors and Activators of ADP-Ribosylation Reactions", *Molec. Cell. Biochem.*, 138:185–97 (1994).

However, the approach of using these PARP inhibitors in the ways discussed above has been limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose that will inhibit the enzyme without producing additional metabolic effects.

The inventors have now discovered that select amino-substituted compounds can inhibit PARP activity and can treat or prevent tissue damage resulting from cell damage or death due to necrosis or apoptosis and/or can ameliorate neural tissue damage, including that following focal ischemia and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and No.

Certain related compounds have been disclosed for medical treatments and other uses. However, these compounds are structurally distinguishable and directed to uses which emphasize their toxic characteristics. Fernandez et al., PCT publication WO 95/29895, discloses an isoquinoline derivative which is used as an anticancer agent. Desilets et al., "Design and Synthesis of Near-Infrared Absorbing Pigments", *Can. J. Chem.* (1995), 73:3, 319–35, disclose the design and synthesis of near-infrared absorbing pigments such as aceanthrene green and derivatives. Langlois et al., "Synthesis of Quinazoline-2,4-dione and Naphthalimide Derivatives as New S-HT$_3$ Receptor Antagonists", *Eur. J. Med. Chem.* (1994), 29:12, 925–940, disclose the preparation and 5-HT$_3$ receptor antagonist activity of certain quinazolinediones, benzisoquinolinones, and -diones. Simmonds, British Patent GB1545767 (1975) disclose benzopyranoisoquinoline derivatives useful for anti-inflammatory and central nervous system activity and also disclose a related compound useful only as an intermediate in making these distinct compounds. Kardos et al., German Patent D.R.P. 282711, disclose structurally distinct but related chlorinated compounds.

Accordingly, there remains a need for a composition containing PARP inhibitors that produce more potent and reliable effects, particularly with respect to treatment of tissue damage resulting from cell death or damage due to necrosis or apoptosis, and less side effects.

SUMMARY OF THE INVENTION

The present invention relates to novel poly(ADP-ribose) polymerase ("PARP") inhibitors and methods for effecting a neuronal activity in an animal using the same. As such, they may treat or prevent neural tissue damage resulting from cell damage or death due to necrosis or apoptosis, cerebral ischemia and reperfusion injury or neurodegenerative diseases in an animal; they may extend the lifespan and proliferative capacity of cells and thus be used to treat or prevent diseases associated therewith; they may alter gene expression of senescent cells; and they may radiosensitize hypoxic tumor cells. Preferably, the compounds of the invention treat or prevent tissue damage resulting from cell damage or death due to necrosis or apoptosis, and/or effect neuronal activity, either mediated or not mediated by NMDA toxicity. These compounds are thought to interfere with more than the glutamate neurotoxicity and NO-mediated biological pathways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune senescence diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging. Preferably, the compounds of the invention exhibit an $IC_{50}$ for inhibiting PARP in vitro of about 100 uM or lower, more preferably, about 25 uM or lower.

Specifically, the present invention relates to a compound of formula I:

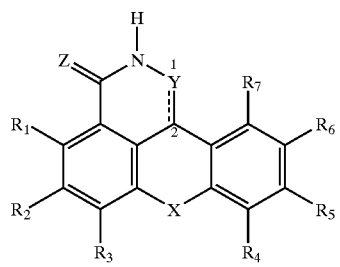

I or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

X is $NR_{16}$, O, S, $CR_{12}R_{13}$, C=O, a bond, —$CR_{12}$=$CR_{13}$—, —$C(R_{12}R_{13})C(R_{14}R_{15})$—, or;

$R_1$, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy; and with the proviso that when Y is CH or $CCH_3$ and there is a double bond between $C_1$ and $C_2$, and $R_1$–$R_7$ are H, then X is not O.

A preferred embodiment of this invention is the compound of formula I, wherein X is O.

Another preferred embodiment of this invention is a compound of formula II:

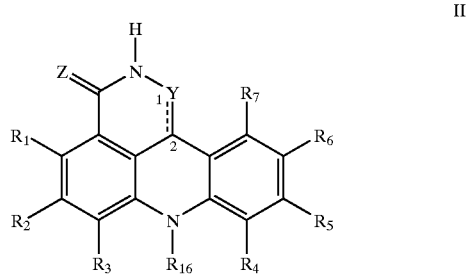

II or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula III:

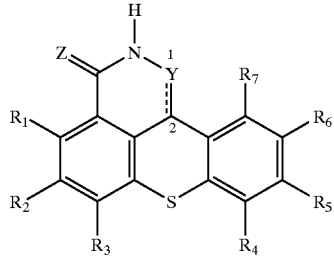

III or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula IV:

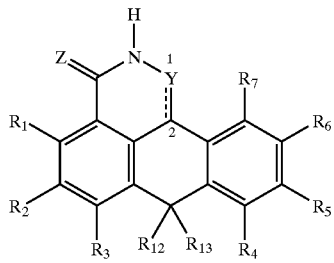

IV or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, $R_{10}$, $R_{12}$, or $R_{13}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula V:

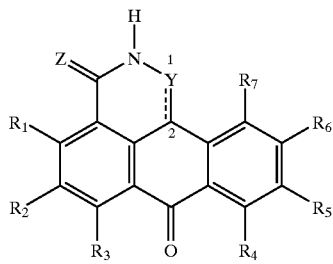

V or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula VI:

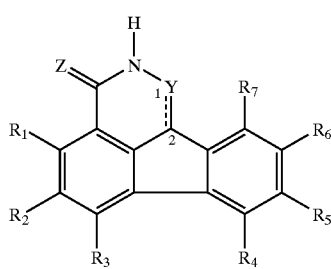

VI or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula VII:

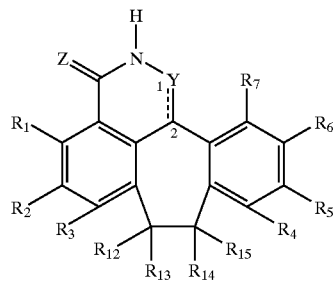

VII or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula VIII:

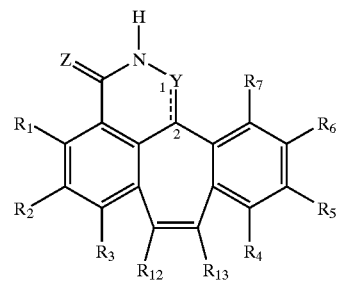

VIII or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

$R_1$, $R_2$, $R_3$, $R_4$, $R_5$, $R_6$, $R_7$, $R_8$, $R_{10}$, $R_{12}$, or $R_{13}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

The following are particularly preferred compounds of the present invention:

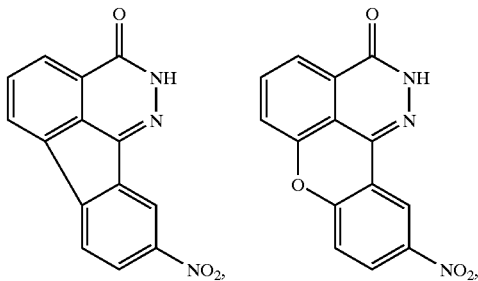
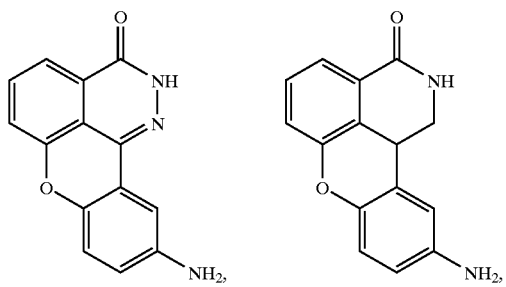
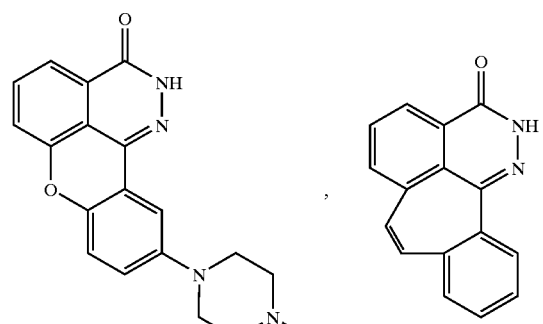
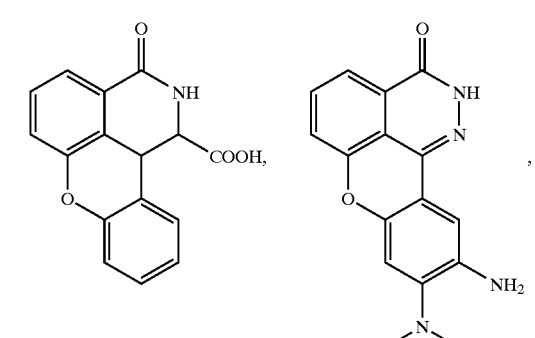
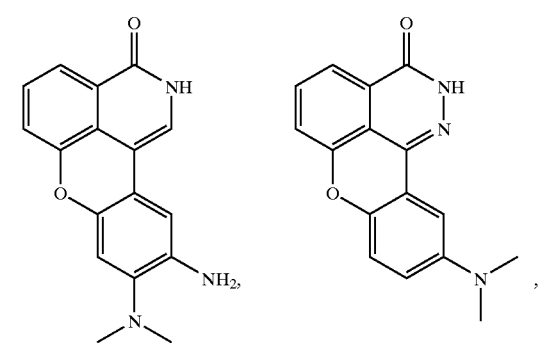
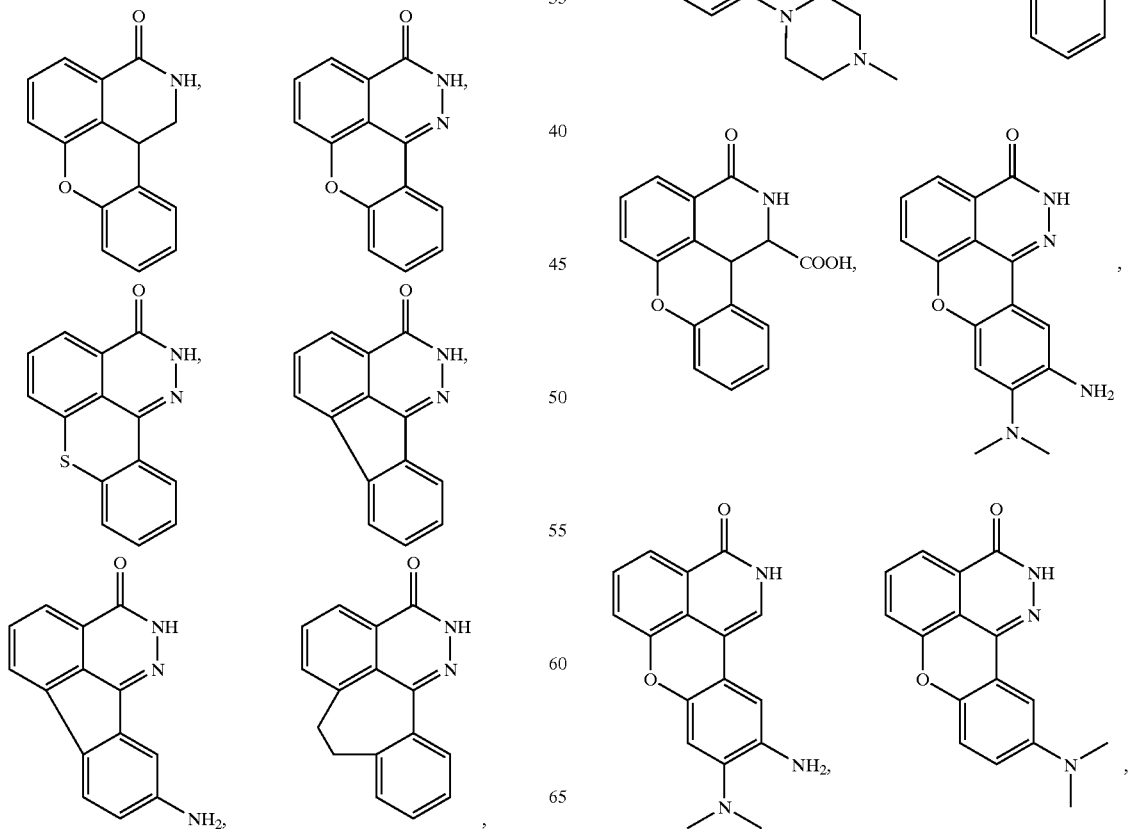

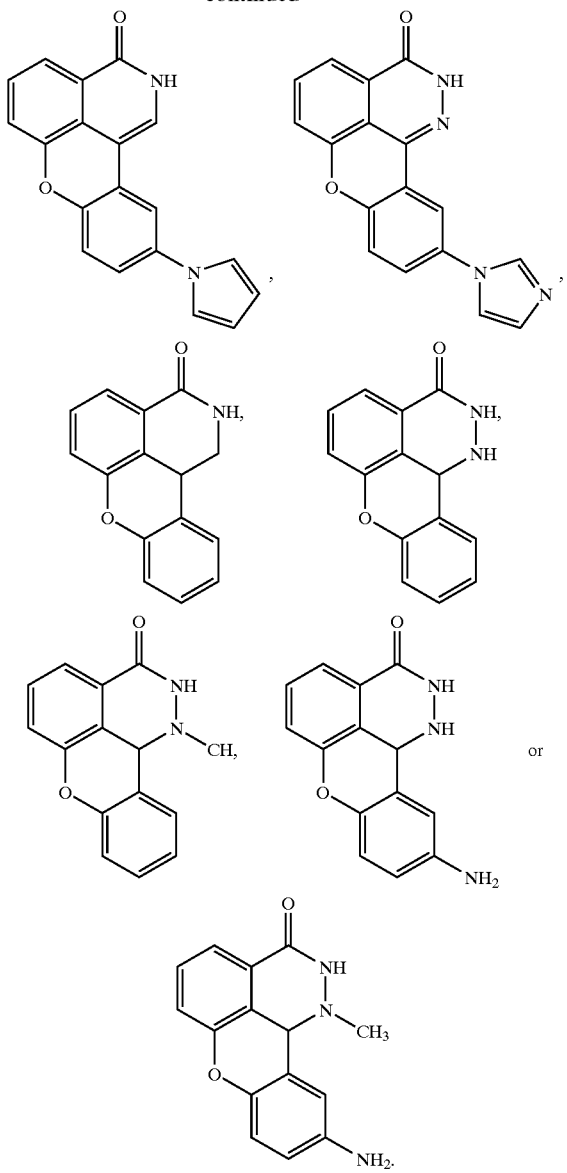

DETAILED DESCRIPTION OF THE INVENTION

Figure 1:
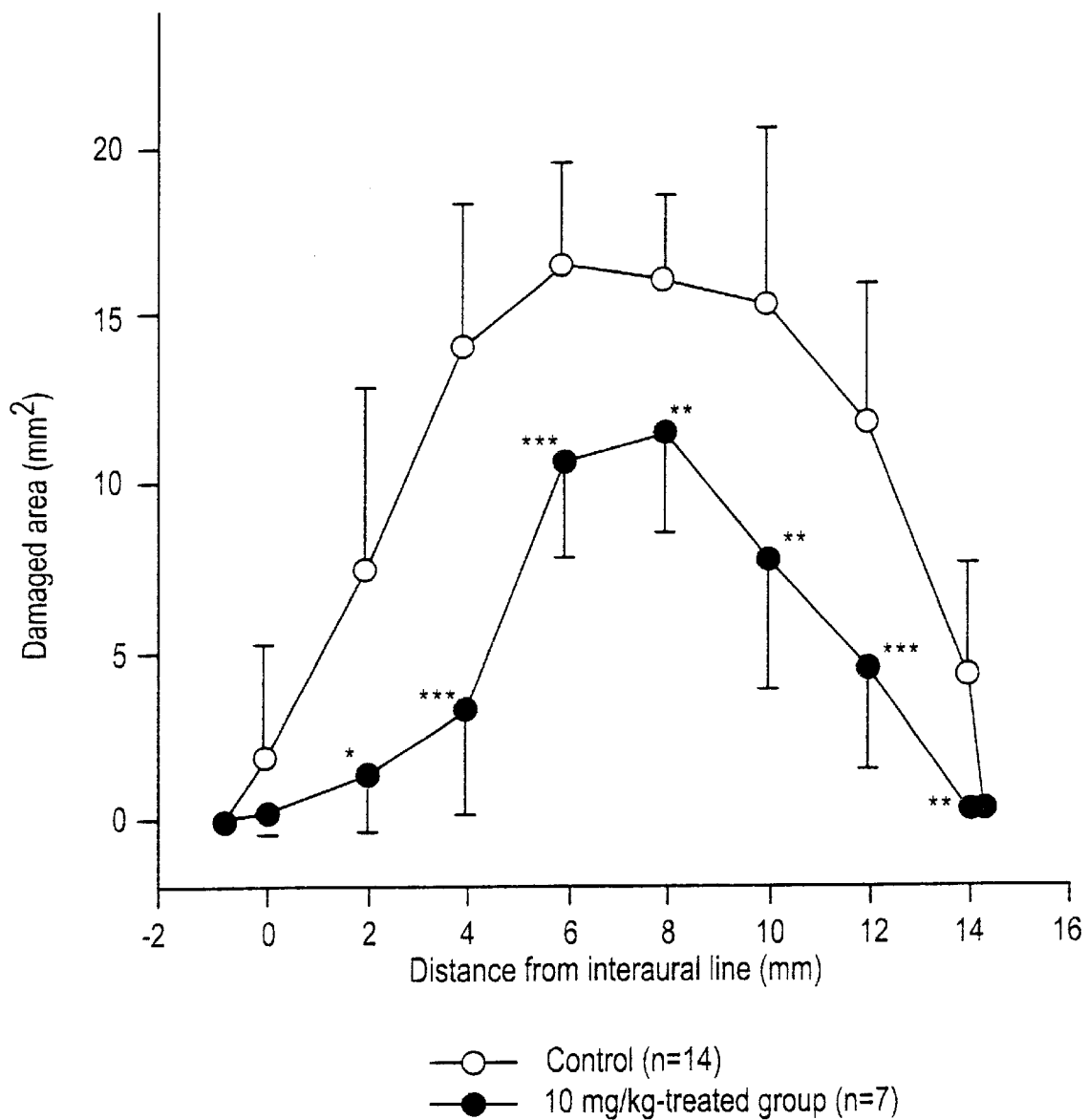
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-botoxyl]-1(2H)-isoquinolinone.

The present invention pertains to compounds, pharmaceutical compositions containing the same, methods of using the same, and process of making the same, wherein such compounds are useful as inhibitors of poly(ADP-ribose) polymerase (PARP). As such, they may treat or prevent neural tissue damage resulting from cell damage or death due to necrosis or apoptosis, cerebral ischemia and reperfusion injury or neurodegenerative diseases in an animal; they may extend the lifespan and proliferative capacity of cells and thus be used to treat or prevent diseases associated therewith; they may alter gene expression of senescent cells; and they may radiosensitize hypoxic tumor cells. Preferably, the compounds of the invention treat or prevent tissue damage resulting from cell damage or death due to necrosis or apoptosis, and/or effect neuronal activity, either mediated or not mediated by NMDA toxicity. These compounds are thought to interfere with more than the glutamate neurotoxicity and NO-mediated biological pathways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune senescence diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging.

Preferably, the compounds of the invention act as PARP inhibitors to treat or prevent tissue damage resulting from cell death or damage due to necrosis or apoptosis; to treat or prevent neural tissue damage resulting from cerebral ischemia and reperfusion injury or neurodegenerative diseases in an animal; to extend and increase the lifespan and proliferative capacity of cells; to alter gene expression of senescent cells; and to radiosensitize tumor cells.

What the inventors have now discovered is that selected PARP inhibitors can ameliorate neural tissue damage and cardiovascular tissue damage, including that following focal ischemia, myocardial infarction, and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO. Preferably, the compounds of the invention exhibit an $IC_{50}$ for inhibiting PARP in vitro of about 100 uM or lower, more preferably, about 25 uM or lower.

Preferred PARP inhibitors of the present invention include compounds having formula I:

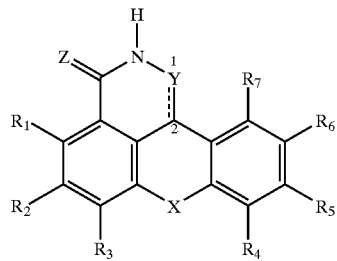

or a pharmaceutically acceptable salt, hydrate, prodrug, or mixtures thereof, wherein Y is alkylhalo, alkyl-CO—G, COG, a direct bond, C=O, O, $NR_{11}$, or $CR_8$;

G is $NR_{11}R_{16}$, $OR_9$, $SR_9$, or $R_{10}$;

Z is O, S, or $NR_{11}$;

X is $NR_{16}$, O, S, $CR_{12}R_{13}$, C=O, a bond, $—CR_{12}=CR_{13}—$, $—C(R_{12}R_{13})C(R_{14}R_{15})—$, or;

$R_1$, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy; and with the proviso that when Y is CH or $CCH_3$ and there is a double bond between $C_1$ and $C_2$, and $R_1$–$R_7$ are H, then X is not O.

Preferred compounds of formula I include those where $R_1$, $R_2$, $R_3$, $R_4$, $R_5$, $R_6$, $R_7$, $R_8$, $R_{10}$, $R_{12}$, $R_{13}$, $R_{14}$, or $R_{15}$ is a substituted or unsubstituted aliphatic or carbocyclic groups; where $R_1$, $R_2$, $R_3$, $R_4$, $R_5$, $R_6$, $R_7$, $R_8$, $R_{10}$, $R_{12}$, $R_{13}$, $R_{14}$, or $R_{15}$ is a heterocyclic groups; where $R_1$, $R_2$, $R_3$, $R_4$, $R_5$, $R_6$, $R_7$, $R_8$, $R_{10}$, $R_{12}$, $R_{13}$, $R_{14}$, or $R_{15}$ is halo, hydroxyl, nitro, 1-piperidine, 1-piperazine, 1-imidazoline, OH, or trifluoromethyl; and where one of $R_1$, $R_2$, or $R_3$ is aryl or aralkyl each having one to five substituents which are independently selected from the group consisting of hydrogen, halo, hydroxyl, amino, alkylamino, double bonded oxygen, carboxy, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula I include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aralkyl or aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or aryl; and where one of $R_4$, $R_5$, $R_6$, or $R_7$ is aryl or aralkyl each having one to five substituents which are independently selected from the group consisting of hydrogen, halo, hydroxyl, amino, alkylamino, aryl, aralkyl, double bonded oxygen, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula I are those where one of $R_4$, $R_5$, $R_6$, or $R_7$ is halo, hydroxyl, nitro, amino, dimethylamino, or trifluoromethyl.

Preferred compounds of formula II include those where
$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula II include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or aryl; and where one of $R_4$, $R_5$, $R_6$, or $R_7$ is aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula II include those where one of $R_4$, $R_5$, $R_6$, or $R_7$ is halo, hydroxyl, amino, dimethylamino, nitro, or trifluoromethyl.

Preferred compounds of formula III include those where
$R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein $R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula III include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; and where one of $R_4$, $R_5$, $R_6$, or $R_7$ is Aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula III include those where one of $R_4$, $R_5$, $R_6$, or $R_7$ is halo, hydroxyl, amino, diemthylamino, nitro, or trifluoromethyl.

Preferred compounds of formula IV include those where $R_1$, $R_2$, $R_3$, $R_4$, $R_5$, $R_6$, $R_7$, $R_8$, $R_{10}$, $R_{12}$, or $R_{13}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

and $R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

and $R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula IV include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; and where one of $R_4$, $R_5$, $R_6$, or $R_7$ is Aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula IV include those where one of $R_4$, $R_5$, $R_6$, or $R_7$ is halo, hydroxyl, nitro, or trifluoromethyl.

Preferred compounds of formula V include those where $R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

and $R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

and $R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula V include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; and where one of $R_4$, $R_5$, $R_6$, or $R_7$ is Aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula V include those where one of $R_4$, $R_5$, $R_6$, or $R_7$ is halo, hydroxyl, nitro, or trifluoromethyl.

Preferred compounds of formula VI include those where
- $R_1$, $R_2$, $R_3$, $R_4$, $R_5$, $R_6$, $R_7$, $R_8$, or $R_{10}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;
- and $R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;
- and $R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula VI include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; and where one of $R_4$, $R_5$, $R_6$, or $R_7$ is Aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula VI include those where one of $R_4$, $R_5$, $R_6$, or $R_7$ is halo, hydroxyl, nitro, or trifluoromethyl.

Preferred compounds of formula VII include those where
- $R_1$, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;
- and $R_9$ is: hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;
- and $R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl; and wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Other preferred compounds of formula VII include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or Aryl; and where one of $R_4$, $R_5$, $R_6$, or $R_7$ is Aryl having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula VII include those where one of $R_4$, $R_5$, $R_6$, or $R_7$ is halo, hydroxyl, nitro, or trifluoromethyl.

Another especially preferred embodiment of the invention is a pharmaceutical composition which comprises (i) a therapeutically effective amount of the compound of formula I; and (ii) a pharmaceutically acceptable carrier.

As used herein, "alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR wherein R is alkyl as herein defined. Preferably, R is a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino groups comprising alkyls of one through six carbons.

"Ar", means an aryl or heteroaryl moiety which is substituted or unsubstituted, especially a cyclic or fused cyclic ring and includes a mono-, bi-, or tricyclic, carbo- or heterocyclic ring, wherein the ring is either unsubstituted or substituted in one to five position(s) with halo, haloalkyl, hydroxyl, nitro, trifluoromethyl, $C_1$–$C_6$ straight or branched chain alkyl, $C_2$–$C_5$ straight or branched chain alkenyl, $C_1$–$C_6$ alkoxy, $C_2$–$C_6$ alkenyloxy, phenoxy, benzyloxy, amino, thiocarbonyl, ester, thioester, cyano, imino, alkylamino, aminoalkyl, sulfhydryl, thioalkyl, and sulfonyl; wherein the individual ring sizes are 5–8 members; wherein the heterocyclic ring contains 1–4 heteroatom(s) selected from the group consisting of O, N, or S; wherein aromatic or tertiary alkyl amines are optionally oxidized to a corresponding N-oxide.

Particularly preferred aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstituted or multi-substituted with substituents selected from the group consisting of amino, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, $(C_1$–$C_6)$-straight or branched chain alkyl, $(C_3$–$C_6)$ straight or branched chain alkenyl or alkynyl, and $(C_1$–$C_4)$ bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

The compounds of the present invention possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is most preferred due to its greater activity.

"Isomers" are different compounds that have the same molecular formula and includes cyclic isomers such as (iso)indole and other isomeric forms of cyclic moieties. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The compounds of the invention may be useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxymethyl)aminoethane; and the like. See, for example, "Pharmaceutical Salts," *J. Pharm. Sci.*, 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor in an aqueous or an, aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are. distributed in and excreted from the body. However, in some cases, metabolism of a drug is required for therapeutic effect. For example, anticancer drugs of the antimetabolite class must be converted to their active forms after they have been transported into a cancer cell. Since must drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are each transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

Phase I Reactions (functionalization reactions):

(1) Oxidation via the hepatic microsomal P450 system:
    Aliphatic oxidation
    Aromatic hydroxylation
    N-Dealkylation
    O-Dealkylation
    S-Dealkylation
    Epoxidation
    Oxidative deamination
    Sulfoxide formation
    Desulfuration
    N-Oxidation and N-hydroxylation
    Dehalogenation
(2) Oxidation via nonmicrosomal mechanisms:
    Alcohol and aldehyde oxidation
    Purine oxidation TABLE II-continued Oxidative deamination (monoamine oxidase and diamine oxidase)
(3) Reduction:
    Azo and nitro reduction
(4) Hydrolysis:
    Ester and amide hydrolysis
    Peptide bond hydrolysis
    Epoxide hydration Phase II Reactions (conjugation reactions):

(1) Glucuronidation
(2) Acetylation
(3) Mercapturic acid formation
(4) Sulfate conjugation
(5) N-, O-, and S-methylation
(6) Trans-sulfuration The compounds of the present invention exhibit pharmacological activity and are, therefore, useful as pharmaceuticals. In particular, the compounds exhibit central nervous and cardiac vesicular system activity.

It is understood that tautomeric forms, when possible, are included in the invention. For example, the tautomeric forms of the following compounds are exemplary:

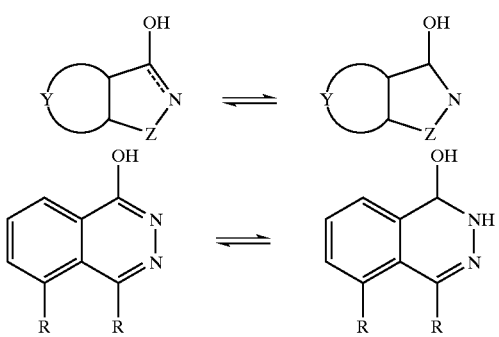

Many of the PARP inhibitors are known and, thus, can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly(ADP-ribose) Polymerase", *Anticancer Drug Des.*, 6:107–17 (1991), which discloses processes for synthesizing a number of different PARP inhibitors.

Typically, the PARP inhibitors used in the composition of the invention will have an $IC_{50}$ for inhibiting poly(ADP-ribose) synthetase in vitro of 100 uM to 0.08 uM, preferably 50 uM to 0.8 uM, more preferably 30 uM to 0.08 uM, more preferably 10 uM to 0.8 uM, more preferably 50 uM to 10 uM, more preferably 30 uM to 10 uM, more preferably 50 uM to 10 uM, more preferably 30 uM to 5 uM, and even more preferably 40 nM to 0.8 uM. The PARP inhibitor 3,4-dihydro-5-[4-(1-piperidinyl)butoxy]-1(2H)-isoquinolinone, for example, has been reported to inhibit PARP with an $IC_{50}$ of 40 nM by Suto et al., cited above.

There are multiple routes which may be undertaken to prepare the compounds of the present invention. Two of these routes for the preparation of the xanthene derivatives of this invention are demonstrated below by schemes 1–3 and 4–7.

The xanthene ring may be generically substituted as set forth in formula I. Such xanthene starting derivatives are known in the chemistry literary and are accessible by processes known to one skilled in the art. The process sequence set forth herein does not present an exact sequence of reactions by which the compound must be made; that is, the sequence of reactions can be rearranged in several ways to reach the target molecule.

9-aminomethylxanthenes are available by reduction of 9-carboxamide using sodium boronhydride in dioxane (Scheme 1). Other reduction methods can be employed, using lithium aluminum hydride or other boronhydrides. The solvent can also be varied: DSISO, tetrahydrofuran, diethylether, and other organic solvent can be used. The temperature of the reaction generally is between 0° C. and 200° C.

Scheme 1

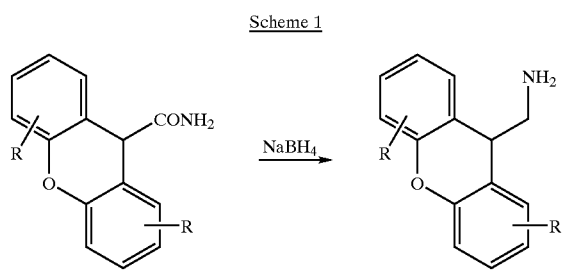

The 9-isocyanomethylxanthene is obtained by condensation of the amino group of the 9-aminomethyl xanthene obtained from Scheme 1 with phosgene in a heated solution of toluene (Scheme 2). Other solvents, such as 1,4-dioxane, chloroform, or p-nitrobenzene, can also be used. The newly formed isocyano functionality serves as an electrophile for the Friedle-Crafts reaction in the next step. Other functionalities including N-carbonylimidazole, N-carbonylbenzotriazole and Nethylformate can also be applied in this type of reaction. In this case, these functionalities can be formed by reaction of the 9-aminomethylxanthenes with carbonyldiimidazole, carbonyldibenzotriazole and ethyl chloroformate respectively.

Scheme 2

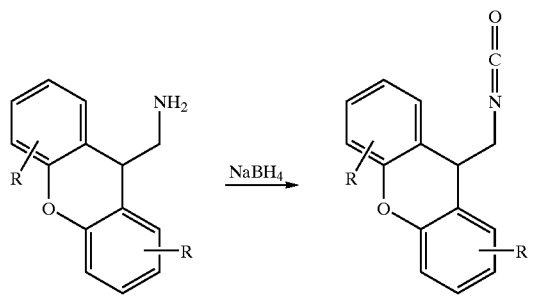

In Scheme 3, the desired xanthene final products can be obtained by an intramolecular Friedle-Crafts acylation using acid as a catalyst. Zinc chloride, aluminum chloride, titanium (IV) chloride, hydrochloric acid, boron trifluoride diethyletherate, or acetic acid may be used, but polyphosphoric acid is often preferred for this type of intramolecular cycloaddition.

Scheme 3

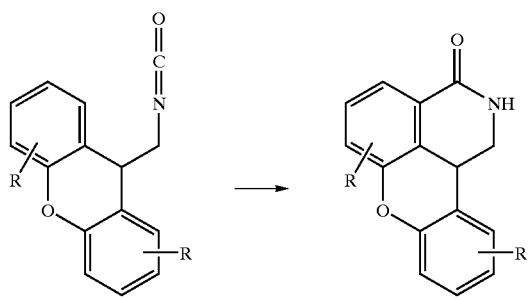

An alternative approach to the preparation of the xanthene derivatives of this invention is illustrated in Schemes 4–7, where the substituent X in Schemes 4–7 can be O, S, or NH.

The starting materials, 3-substituted orthophenyldinitriles or 3-substituted orthophenyldicarboxylic acids, are either readily available or can be prepared by known methods by those skilled in the art. The formation of orthocarbonyl groups from the cyano groups can be achieved by hydrolysis of the aryl nitrile with mineral acids, such as sulphoric acids and hydrochloric acids (Scheme 4). Hydrolysis of the nitrile with sodium hydroxide solution, followed by acidification, can also yield the corresponding acid.

Scheme 4

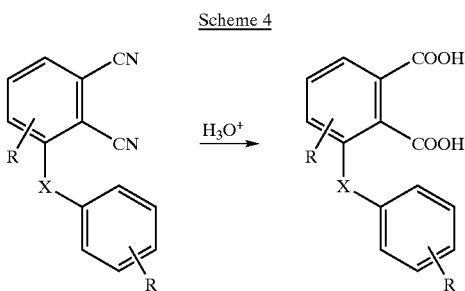

An intramolecular Friedle-Crafts acylation using Lewis acids or polyphosphonic acids as catalysts can provide the xanthene (X=O), acridine (X=NH) or thioxanthene (X=S) skeleton (Scheme 5). This reaction can be run in a regioselective manner determined by R substitutional groups.

Scheme 5

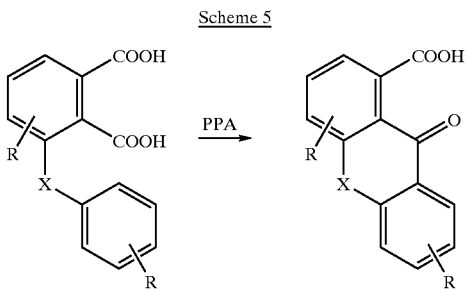

Esterification of the acid of Scheme 5 can be achieved by those skilled in the art through the use of any one of several conventional methods. One of these procedures includes the utilization of diazomethane (Scheme 6). Another similar procedure involves the use of methyl alcohol catalyzed by mineral acids.

Scheme 6

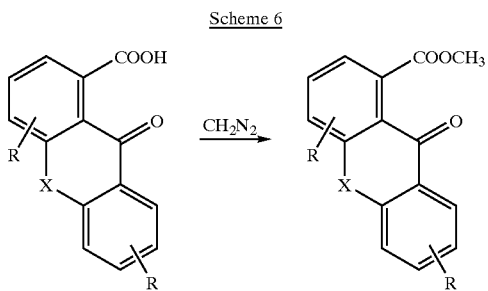

In Scheme 7, the phthalazine ring (Y=NHN=) can be formed by condensation of the ketone ester obtained from Scheme 6 with hydrazine. Hydrogenation of the phthalazine derivative with a catalyst provides the acyl hydrazide (Y=NHNH). Similarly, when the ketone ester reacts with hydroxyamine, the result is a cyclized hydroxymic acid derivative (Y=NH—O). The lactams (Y=NH) can also be made by cycloaddition of the ketone ester with ammonium acetate in acetic acid. Other single amino sources, including ammonia, can be used to replace ammonium acetate.

Scheme 7

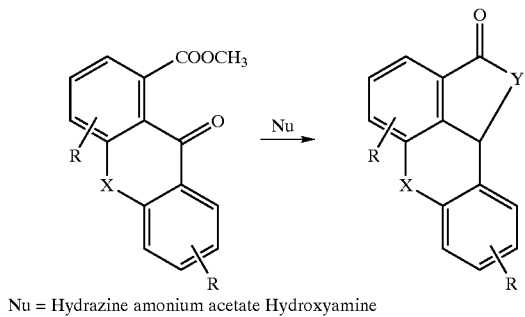

Nu = Hydrazine amonium acetate Hydroxyamine

Methods of Using the Compounds of the Invention

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; and can radiosensitize cells. Generally, inhibition of PARP activity spares the cells from energy loss, preventing irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

Yet another preferred embodiment is a method of treating, preventing or inhibiting a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of compound I, II, III, IV, V, VI, VII, or VIII for inhibiting PARP activity, for treating, preventing or inhibiting tissue damage resulting from cell damage or death due to necrosis or apoptosis, for treating, preventing or inhibiting a neurological disorder in an animal.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The present invention also contemplates the use of compound I, II, III, IV, V, VI, VII, or VIII in the preparation of a medicament for the treatment of any of the diseases and disorders in an animal described herein.

In a particular embodiment, the disease or disorder is a neurological disorder.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome.

Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease, Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-10}$ to $10^0$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Compositions and Methods for Effecting Neuronal Activity

Preferably, the compounds of the invention inhibit PARP activity and, thus, are believed to be useful for treating neural tissue damage, particularly damage resulting from cerebral ischemia and reperfusion injury or neurodegenerative diseases in animals. The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures. Further, according to the invention, an effective therapeutic amount of the compounds and compositions described above are administered to animals to effect a neuronal activity, particularly one that is not mediated by NMDA neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of the compound of formula I to said animal.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's Disease and Parkinson's disease. The term "neurodegenerative diseases" includes Alzheimer's disease, Parkinson's disease and Huntington's disease. The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

The method of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Alzheimer's Disease, Parkinson's Disease, Huntington's Disease and amyotrophic lateral sclerosis (ALS).

The term "neural tissue damage resulting from ischemia and reperfusion injury and neurodegenerative diseases" includes neurotoxicity, such as seen in vascular stroke and global and focal ischemia.

Treating Other PARP-Related Disorders

The compounds, compositions and methods of the present invention are particularly useful for treating or preventing tissue damage resulting from cell death or damage due to necrosis or apoptosis.

The compounds, compositions and methods of the invention can also be used to treat a cardiovascular disorder in an animal, by administering an effective amount of the compound of formula to the animal. As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

For example, the methods of the invention are believed to be useful for treating cardiac tissue damage, particularly damage resulting from cardiac ischemia or caused by reperfusion injury in animals. The methods of the invention are particularly useful for treating cardiovascular disorders selected from the group consisting of: coronary artery disease, such as atherosclerosis; angina pectoris; myocardial infarction; myocardial ischemia and cardiac arrest; cardiac bypass; and cardiogenic shock. The methods of the invention are particularly helpful in treating the acute forms of the above cardiovascular disorders.

Further, the methods of the invention can be used to treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of: gamma-radiation ($10^{-10}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers (e.g., 2-nitroimidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

The compounds of the present invention may also be used for radiosensitizing tumor cells.

The term "treating" refers to:
  (i) preventing a disease, disorder or condition from occurring in an animal that may be predisposed to the disease, disorder and/or condition, but has not yet been diagnosed as having it;
  (ii) inhibiting the disease, disorder or condition, i.e., arresting its development; and
  (iii) relieving the disease, disorder or condition, i.e., causing regression of the disease, disorder and/or condition.

Pharmaceutical Compositions of the Invention

The present invention also relates to a pharmaceutical composition comprising (i) a therapeutically effective amount of the compound of formula I, II, III, IV, V, VI, VII, or VIII, and (ii) a pharmaceutically acceptable carrier.

An especially preferred embodiment of the invention is a pharmaceutical composition which comprises (i) a therapeutically effective amount of a compound of formula I; and (ii) a pharmaceutically acceptable carrier.

Another especially preferred embodiment of the invention is a pharmaceutical composition which comprises (i) a therapeutically effective amount of a compound of formula II; and (ii) a pharmaceutically acceptable carrier.

Another especially preferred embodiment of the invention is a pharmaceutical composition which comprises (i) a therapeutically effective amount of a compound of formula III; and (ii) a pharmaceutically acceptable carrier.

Another especially preferred embodiment of the invention is a pharmaceutical composition which comprises (i) a therapeutically effective amount of a compound of formula IV; and (ii) a pharmaceutically acceptable carrier.

Yet another especially preferred embodiment of the invention is a pharmaceutical composition which comprises (i) a therapeutically effective amount of a compound of formula V; and (ii) a pharmaceutically acceptable carrier.

Yet another especially preferred embodiment of the invention is a pharmaceutical composition which comprises (i) a therapeutically effective amount of a compound of formula VI; and (ii) a pharmaceutically acceptable carrier.

Another especially preferred embodiment of the invention is a pharmaceutical composition which comprises (i) a therapeutically effective amount of a compound of formula VII; and (ii) a pharmaceutically acceptable carrier.

Another especially preferred embodiment of the invention is a pharmaceutical composition which comprises (i) a therapeutically effective amount of the compound of formula VIII; and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly (hydroxyethylmethacrylate) or poly(vinylalcohol) also may be useful, but for shorter release cycles than the other polymer release systems, such as those mentioned above.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. Said compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. Said compositions are prepared according to conventional mixing, granulating, or coating methods, and contain about 0.1 to 75%, preferably about 1 to 50%, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to inhibit PARP and derive the beneficial effects therefrom through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The present invention relates to the use of compounds I, II, III, IV, V, VI, VII, or VIII in the preparation of a medicament for the treatment of any disease or disorder in an animal described herein.

PARP Assay

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting. The compounds of this invention were found to have potent enzymatic activity in the range of a few NM to 20 M in $IC_{50}$ in this inhibition assay.

Focal cerebral ischemia experiments were performed using male Wistar rats weighing 250–300 g which were anesthetized with 4% halothane. This anesthesia was maintained with 1.0–1.5% halothane until the end of the surgery. The animals were placed in a warm environment to avoid a decrease of body temperature during surgery. An anterior midline cervical incision was made. The right common carotid artery (CCA) was exposed and was isolated from the vagus nerve. A silk suture was placed and tied around the CCA in proximity to the heart. The external carotid artery (ECA) was then exposed and was ligated with a silk suture. A puncture was made in the CCA and a small catheter (PE 10, Ulrich & Co., St-Gallen, Switzerland) was gently advanced to the lumen of the internal carotid artery (ICA). The pterygopalatine artery was not occluded. The catheter was tied in place with a silk suture. Then, a 4-0 nylon suture (Braun Medical, Crissier, Switzerland) was introduced into the catheter lumen and was pushed until the tip blocked the anterior cerebral artery. The length of catheter advanced into the ICA was approximately 19 mm from the origin of the ECA. The suture was maintained in this position by occlusion of the catheter by heat. One cm of catheter and nylon suture were left protruding so that the suture could be withdrawn to allow reperfusion. The skin incision was then closed with wound clips and the animals maintained in a warm environment during recovery from anesthesia. Two hours later, the animals were re-anesthized, the clips were discarded and the wound re-opened. The catheter was cut and the suture was pulled out. The catheter was then obturated again by heat, and wound clips were placed on the wound. The animals were allowed to survive for 24 hours with free access to food and water. The rats were sacrificed with $CO_2$ and were decapitated. The brains were immediately removed, frozen on dry ice and stored at −80° C. The brains were then cut in 0.02 mm-thick sections in a cryocut at −19° C., taking one of every 20 sections. The sections were stained with cresyl violet according to the Nissl procedure. Each section was examined under a light microscope and the regional infarct area was determined according to the presence of cells with morphological changes. Various doses of compounds were tested in this model. The compounds were given in either single or multiple doses, i.p. or i.v., at different times before or after the onset of ischemia. Compounds of this invention were found to have protection in the range of 20 to 80 per cent in this assay.

The experiments of the heart ischemia/reperfusion injury model were performed using female Sprague-Dawley rats weighing 300–350 g which were anesthetized with intraperitoneal ketamine at a dose of 150 mg/kg. The rats were endotracheally incubated and ventilated with oxygen-enriched room air using a Harvard rodent ventilator. Polyethylene catheters inserted into the carotid artery and the femoral vein were used for artery blood pressure monitoring and fluid administration, respectively. Arterial $pCO_2$ was maintained between 35 and 45 mmHg by adjusting the respiratory rate. The rat chests were opened by median sternotomy, the pericardium was incised, and the hearts were cradled with a latex membrane tent. Hemodynamic data were obtained at baseline after at least 15 minute stabilization from the end of the surgical operation. The LAD (left anterior descending) coronary artery was ligated for 40 minutes and was followed by 120 minutes of reperfusion. After 120 minutes of reperfusion, the LAD artery was reoccluded, and a 0.1 ml bolus of monastral blue dye was injected into the. left atrium to determine the ischemic risk region. The hearts were then arrested with potassium chloride. The hearts were cut into five 2-3 mm thick transverse slices, and each slice was weighed. The sections were incubated in a 1% solution of triphenyltetrazolium chloride to visualize the infarcted myocardium located within the risk region. Infarct size was calculated by summing the values for each left ventricular slice and expressed as a fraction of the risk region of the left ventricle. Various doses of compounds were tested in this model. The compounds were given in either single or multiple doses, i.p or i.v., at different times before or after the onset of ischemia. The compounds of this invention were found to have ischemia/reperfusion injury protection in the range of to 40 percent in this assay.

As a result of their demonstrated PARP inhibition, the compounds of this invention protect against ischemia-induced degeneration of rat hippocampal neurons in vitro and thus may be useful in disorders arising from cerebral ischemia such as stroke, septic shock, or CNS degenerative disorders. They may also be useful in protecting the spinal cord following trauma. As an experimental result of ischemia/reperfusion injury in rats, the present invention is further directed to a method of prophylactic or therapeutic treatment of heart attack, cardiac arrest, cardiac bypass, diabetes, or risk of damage which comprises administering an effective amount of a compound of the present invention for PARP inhibition in unit dosage form.

EXAMPLES

Example 1

Preparation of 9-aminomethylxanthene

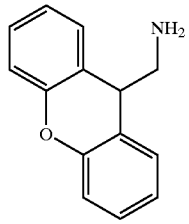

To a stirred suspension of sodium boronhydride (1.89 g, 50 mmol) and 9-xanthencarboxamide (2.25 g, 10 mmol) in dioxane (20 mL) was added acetic acid (3.0 g, 50 mmol) in dioxane (10 mL) over a period of 10 minutes at 10° C.; the reaction mixture was stirred at reflux for 2 hours. The reaction mixture was concentrated to dryness in vacuo, excess reagent was decomposed with water and the solution extracted with chloroform. The extract was washed with water and dried over anhydrous sodium sulphate. The chloroform layer was evaporated in vacuo and the residue was purified by silica gel column chromatography (ethylacetate:methanol, 9:1 as eluent) to give a white solid (1.6 g, 7.6 mmol) in 76.2% yield.

Example 2

Preparation of xanthenyl-9-methylisocyanate

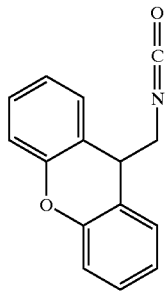

To a stirred solution of 9-aminomethylxanthene (2.11 g, 10 mmol) (see Example 1) in anhydrous 1,4-dioxane (150 mL) was added triphosgene (97.9 mg, 0.33 mmol) at room temperature. The solution was heated at reflux for four hours and then cooled to room temperature. Diethyl ether (200 mL) and water (100 mL) were added to the solution. The organic layer was washed with saturated sodium bicarbonate (50 mL), water (2×50 mL) and brine (200 mL). The organic layer collected was dried over sodium sulfate. The solvent was removed to give an oil residue (2.38 g) without further purification for use in the next step.

Example 3

Preparation of [1] 1,11b-Dihydrobenzopyrano[4,3,2-de]isoquinolin-3-one

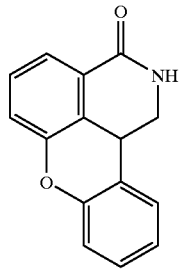

Polyphosphoric acid (12 g) was heated to 90° C. in a 500 mL beaker placed in an oil bath. The xanthenyl-9-methylisocyanate of Example 2 (2.37 g, 10 mmol) was added to the liquid acid portion-wise with manual stirring at 90° C. The mixture was stirred for three minutes and then an additional 100 g of the polyphosphoric acid were added. Vigorous stirring was applied for four minutes while the temperature was kept at 90° C. The mixture was allowed to cool to 60° C. and 40 g crushed ice was added until the polyphosphoric acid was completely hydrolyzed and a brown solid was separated. The solid was collected by vacuum filtration and then recrystallized in chloroform chloride to afford a desired product (1.5 g, 6.33 mmol) in 63% yield.

Example 4

Preparation of 3-phenoxybenzene-1,2-dicarboxylic acid

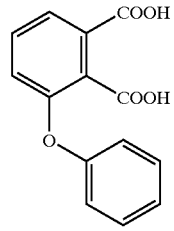

60 g of 75 per cent sulfuric acid was prepared by adding 45 g (24 ml) of concentrated sulfuric acid cautiously, with stirring and cooling, to 15 ml of water. The latter was placed in a 0.5-liter three-necked flask, equipped with a dropping funnel, a mechanical stirrer, and a reflux condenser. The solution was heated in an oil bath to about 120° C., and nitrite (22 g, 100 mmol) was added with stirring during a period of 0.2 hours. The stirring was- continued for a further 1 hour while the temperature was maintained at 120° C. The temperature was then allowed to rise to 150° C., and the solution was stirred for another hour. The reaction mixture was cooled and poured into ice-cold water. The precipitated acid was collected by filtration. The crude acid was dissolved in an excess of 10 per cent sodium hydroxide solution, and insoluble material was filtered through a sintered glass funnel while still hot. The filtrate was acidified with dilute sulfuric acid. The solid acid was collected on a Buchner funnel, and dried in the air. The yield of crude acid was (15 g, 78 mmol) 78 per cent.

Example 5

Preparation of 9-oxoxanthene-1-carboxylic acid

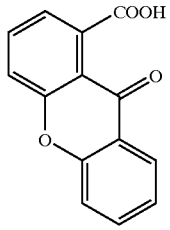

12 g of polyphosphoric acid was heated to 90° C. in a 500 mL beaker placed in an oil bath. The diacid of Example 4 (2.58 g, 10 mmol) was added to the liquid acid portion wise with manual stirring at 100° C. The mixture was stirred for three. minutes and then 100 g more of the polyphosphoric acid was added. Vigorous stirring was applied for four minutes while the temperature was kept at 90° C. The mixture was allowed to cool to 60° C. and 40 g of crushed ice was added until the polyphophoric acid was completely hydrolyzed and a yellow oil was separated. The mixture was extracted with three 150 mL portions of methylene chloride and the combined extracts were washed with water, 5 percent aqueous sodium hydroxide solution, and then water until the washings were neutral. The organic layer was dried over magnesium sulfate and the solvent was removed on a rotary evaporator. Purification of this residue on a silica gel column provided the desired product as a solid (1.68 g, 7.0 mmol) in 70% yield.

Example 6

Preparation of 9-oxoxanthene-1-methylcarboxylate

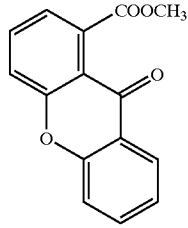

2.14 g of N-methyl-N-nitrosotoluene-p-sulphonamide was dissolved in 30 ml of ether and cooled in ice. A solution of 0.4 g of potassium hydroxide in 10 ml of 96 per cent ethanol was added. If a precipitate forms, add more ethanol until it just dissolves. After 5 minutes, the ethereal diazomethane solution was distilled from a water bath. The ethereal solution contained 0.32–0.35 g of diazomethane. The 9-oxoxanthene-1-carboxylic acid of Example 5 (1.29 g, 5 mmol) was dissolved in absolute methanol, cooled to 0° C., and the ethereal solution of diazomethane was added in a small portion until gas evolution ceased. The solution showed a pale yellow color. The desired ester was obtained by removal of the solvent in vacuum to give a clear oil (1.36 g, 5 mmol) in 100% yield.

Example 7

Preparation of [1] 1,2,3,11b-tetrahydrobenzopyrano [4,3,2-de]phthalazin-3-one, and (2H) benzopyrano [4,3,2-de]phthalazin-3-one

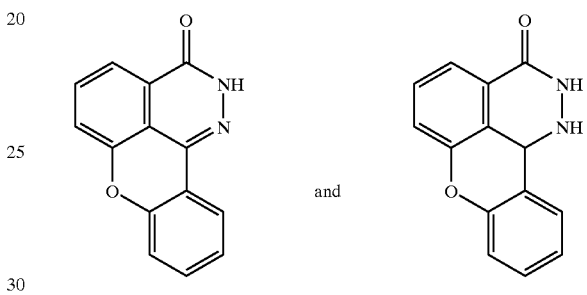

Synthesis of (2H) benzopyrano[4,3,2-de]phthalazin-3-one

To a solution of the ester of Example 6 (1.36 g, 5 mmol) in absolute ethanol (10 mL) was added anhydrous hydrazine in ethanol (1 mL) drop wise at room temperature. The solution was refluxed overnight and cooled to room temperature. Ice-cold water (100 mL) was added and gray solid was separated. The solid was collected by vacuum filtration and washed with water to provide (2H) benzopyrano [4,3, 2-de]phthalazin-3-one.

Synthesis of [1] 1,2,3,11b-tetrahydrobenzopyrano[4,3,2-delphthalazine-3-one

The solid was dissolved in glacial acetic acid (100 mL) and the solution was placed in a hydrogenation bomb. Palladium (10% on carbon, 500 mg) was added. The bomb was set at a pressure of 2000 psi and stirred for 20 hours. The mixture of the content was poured through a fluted filter paper to remove the catalyst. The solvent of the filtrate was removed in vacuo to give a yellow solid which was recrystallized in chloroform to afford the desired product (0.95 g, 4.0 mmol) in 80% yield.

Example 8

Preparation of [1]1,10b dihydrobenzopyrano[4,3,2-de]isoindolin-1-one

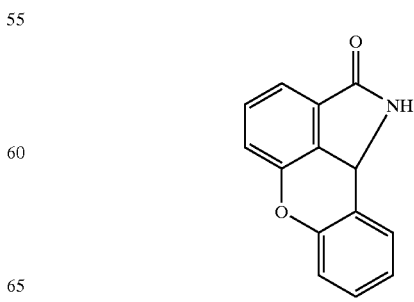

A mixture of ammonium acetate (115 mg, 1.5 mmol), glacial acetic acid (1.5 mL) and the 9-oxoxanthene-1-methylcarboxylate of Example 6 (272 mg, 1.0 mmol) was refluxed for six hours. The solution was placed in a hydrogenation bomb with additional acetic acid (10 mL) added. Palladium (10% on carbon, 100 mg) was added. The bomb was set at a pressure of 2000 psi and stirred for 20 hours. The mixture of the content was poured through a fluted filter paper to remove the catalyst. The solvent of the filtrate was removed in vacuo to give a solid which was recrystallized in chloroform to afford the desired product (66 mg, 0.3 mmol) in 30% yield.

Example 9

Preparation of [2]3,11b-Dihydroxantheno[1,9-de][1,2]oxazin-3-one

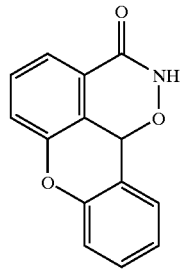

To a solution of the ester of Example 6 (1.36 g, 5 mmol) in absolute ethanol (10 mL) was added anhydrous hydrazine in ethanol (1 mL) drop wise at room temperature. The solution was refluxed overnight and cooled to room temperature. Ice-cold water (100 mL) was added and brown solid was separated. The solid was collected by vacuum filtration and washed with water.

A solution of this crude solid hydroxamic acid in acetic acid (100 mL) was placed in a high pressure bomb, 5 mL of settled Raney nickel catalyst was added, the cap was securely fastened and hydrogen gas was introduced until the pressure was 1000 psi. The mechanical stirring device was set in motion and the reaction was allowed to proceed overnight. The mixture of the content was poured through a fluted filter paper to remove the catalyst (do not permit the catalyst to become dry since it is likely to ignite). Removal of the solvent of the filtrate gave a brown solid which was recrystallized in chloroform to afford the desired product (0.24 g, 1.0 mmol) in 25% yield.

Example 10

Preparation of [1] 1,3,11b-Trihydro benzopyrano[4,3,2-de]isoquinolin-1,3-dione

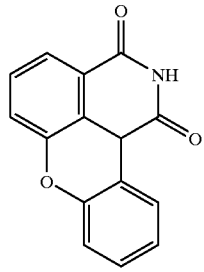

As Example 9.

Example 11

Approximate $IC_{50}$ Data for Selected Compounds

The $IC_{50}$ of with respect to PARP inhibition was determined for several compounds by a PARP assay using purified recombinant human PARP from Trevigen (Gaithersburg, Md.), as follows: The PARP enzyme assay was set up on ice in a volume of 100 microliters consisting of 10 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction was initiated by incubating the mixture at 25° C. After 15 minutes' incubation, the reaction was terminated by adding 500 microliters of ice cold 20% (w/v) trichloroacetic acid. The precipitate formed was transferred onto a glass fiber filter (Packard Unifilter-GF/B) and washed three times with ethanol. After the filter was dried, the radioactivity was determined by scintillation counting.

Using the PARP assay described above, approximate $IC_{50}$ values were obtained for the following compounds:

| Compound | $IC_{50}$ (uM) |
|---|---|
| | 0.20 |
| | 0.08 |
| | 0.11 |

-continued

| Compound | IC$_{50}$ (uM) |
|---|---|
| (structure) | 0.14 |
| (structure with NH$_2$) | 0.068 |
| (structure) | 0.4 |
| (structure with NO$_2$) | 0.056 |
| (structure with NO$_2$, O) | 0.062 |

-continued

| Compound | IC$_{50}$ (uM) |
|---|---|
| (structure with O, NH$_2$) | 0.046 |
| (structure with O, NH$_2$) | 0.5–5.0 |
| (structure with O, N-methylpiperazine) | 0.5–5.0 |
| (structure) | 0.20–1.5 |
| (structure with O, COOH) | 0.20–1.2 |

| Compound | IC₅₀ (uM) |
|---|---|
| (structure) | 0.08–2.0 |
| (structure) | 0.01–3.0 |
| (structure) | 0.10–3.0 |
| (structure) | 0.10–3.0 |
| (structure) | 0.10–3.0 |
| (structure) | 0.20–1.2 |
| (structure) | 0.08–2.0 |
| (structure) | 0.01–3.0 |
| (structure) | 0.10–3.0 |

-continued

| Compound | IC$_{50}$ (uM) |
|---|---|
| [structure with O, NH, N-CH$_3$, O, NH$_2$ groups] | 0.10–3.0 |

Similar IC$_{50}$ values are obtained for the amino-substituted compounds of the invention.

Example 12

Neuroprotective Effect of DPQ on Focal Cerebral Ischemia in Rats

Focal cerebral ischemia was produced by cauterization of the right distal MCA (middle cerebral artery) with bilateral temporary common carotid artery occlusion in male Long-Evans rats for 90 minutes. All procedures performed on the animals were approved by the University Institutional Animal Care and Use Committee of the University of Pennsylvania. A total of 42 rats (weights: 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound, 3,4-dihydro-5-[4-(1-piperidinyl)-butoxy]-1(2H)-isoquinolinone ("DPQ") were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%–1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, PaO$_2$ and PaCO$_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagittal suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", *Stroke* 17:738–43 (1986) and/or Liu et al., "Polyethylene Glycol-conjugated Superoxide Dismutase and Catalase Reduce Ischemic Brain Injury", *Am. J. Physiol.* 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2% 2,3,5-triphenyltetrazolium chloride (TTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", *J. Cereb. Blood Flow Metabol.* 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-(4-(1-piperidinyl)-butoxy]-1(2H)-isoquinolinone. The area of damage was expressed as mean±standard deviation. Significant differences between the 10 mg-treated group and the control group were indicated ($^+p<0.02$, $^{++}p<0.01$, $^{++}p<0.001$). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group ($106.7\pm23.2$ mm$^3$, $p<0.001$), the 10 mg/kg-treated group ($76.4\pm16.8$ mm$^3$, $p<0.001$), and the 20 mg/kg-treated group ($110.2\pm42.0$ mm$^3$, $p<0.01$), compared to the control group ($165.2\pm34.0$ mm$^3$. The data are expressed as mean±standard deviation. The significance of differences between groups was determined using an analysis of variance (ANOVA) followed by Student's t-test for individual comparisons.

There was no significant difference between the control and the 40 mg/kg-treated group ($135.6\pm44.8$ mm$^3$). However, there were significant differences between the 5 mg/kg-treated group and the 10 mg/kg-treated group ($p<0.02$), and between the 10 mg/kg-treated group and the 40 mg/kg-treated group ($p<0.01$), as shown in FIG. 2.

Figure 2:
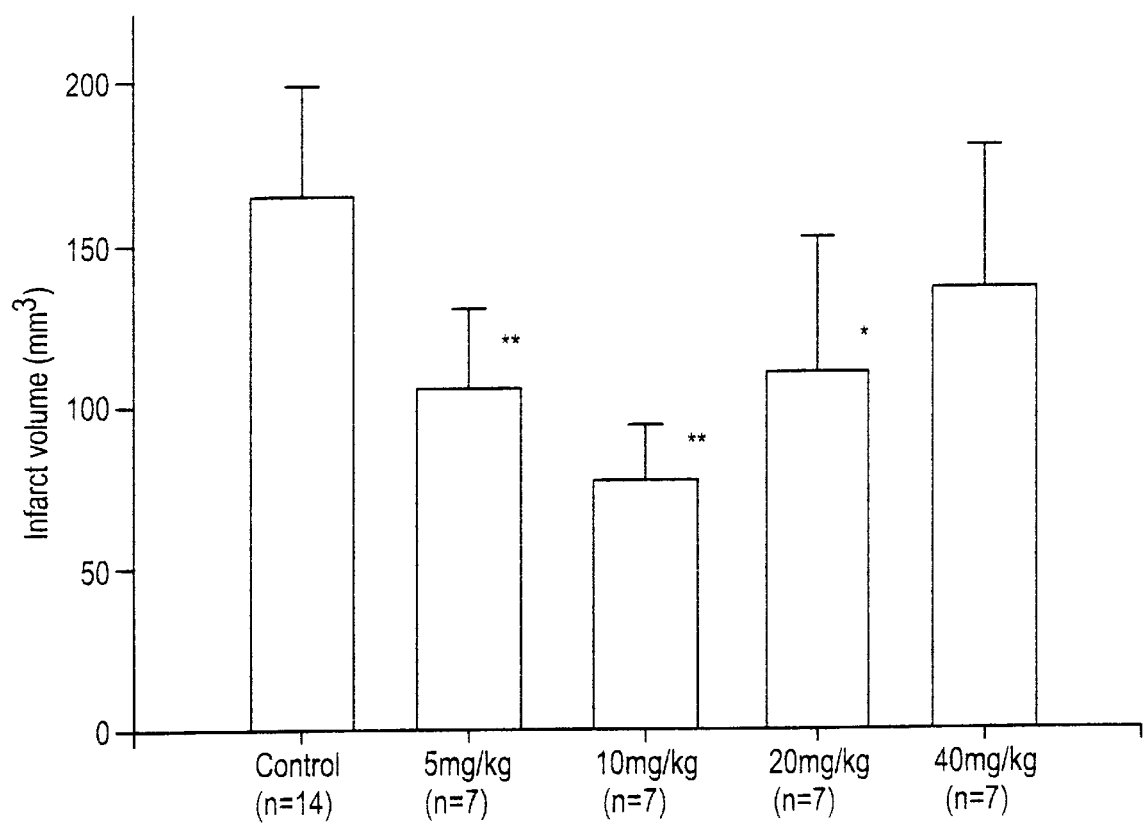
FIG. 2 shows the effect of intraperitoneal administration of 3,4-dihydro-5-[4-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean±standard deviation. Significant differences between the treated groups and the control group were indicated ($^+p<0.01$, $^{++}p<0.001$). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases (PaO$_2$, PaCO$_2$ and pH) were within the physiological range in the control and treated groups with no significant differences in these parameters among the five groups, as shown below in Table 2. A "steady state" MABP was taken following completion of the surgical preparation, just prior to occlusion; an "ischemia" MABP was taken as the average MABP during occlusion. See Table III below:

TABLE III

| | PaO$_2$ (mm Hg) | PaCO$_2$ (mm Hg) | pH | MABP (mm Hg) | |
| --- | --- | --- | --- | --- | --- |
| | | | | Steady State | Ischemia |
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

*= Significantly different from the steady state value, $p < 0.05$.
**= Significantly different from the steady state value, $p < 0.01$.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

This example provided evidence that the related compounds of the present invention are effective in inhibiting PARP activity.

Example 13

Assay for Neuroprotective Effects on Focal Cerebral Ischemia in Rats

Focal cerebral ischemia experiments are performed using male Wistar rats weighing 250–300 g, which are anesthetized with 4% halothane. Anesthesia is maintained with 1.0–1.5% halothane until the end of surgery. The animals are installed in a warm environment to avoid a decrease in body temperature during surgery.

An anterior midline cervical incision is made. The right common carotid artery (CCA) is exposed and isolated from the vagus nerve. A silk suture is placed and tied around the CCA in proximity to the heart. The external carotid artery (ECA). is then exposed and ligated with a silk suture. A puncture is made in the CCA and a small catheter (PE 10, Ulrich & Co., St-Gallen, Switzerland) is gently advanced to the lumen of the internal carotid artery (ICA). The pterygopalatine artery is not occluded. The catheter is tied in place with a silk suture. Then, a 4-0 nylon suture (Braun Medical, Crissier, Switzerland) is introduced into the catheter lumen and is pushed until the tip blocks the anterior cerebral artery. The length of catheter into the ICA is approximately 19 mm from the origin of the ECA. The suture is maintained in this position by occlusion of the catheter with heat. One cm of catheter and nylon suture are left protruding so that the suture can be withdrawn to allow reperfusion. The skin incision is then closed with wound clips.

The animals are maintained in a warm environment during recovery from anesthesia. Two hours later, the animals are re-anesthetized, the clips are discarded, and the wound is re-opened. The catheter is cut, and the suture is pulled out. The catheter is then obturated again by heat, and wound clips are placed on the wound. The animals are allowed to survive for 24 hours with free access to food and water. The rats are then sacrificed with $CO_2$ and decapitated.

The brains are immediately removed, frozen on dry ice and stored at $-80°$ C. The brains are then cut in 0.02 mm-thick sections in a cryocut at $-19°$ C., selecting one of every 20 sections for further examination. The selected sections are stained with cresyl violet according to the Nissl procedure. Each stained section is examined under a light microscope, and the regional infarct area is determined according to the presence of cells with morphological changes.

Various doses of the compounds of the invention are tested in this model. The compounds are administered in either a single dose or a series of multiple doses, i.p. or i.v., at different times, both before or after the onset of ischemia. Compounds of the invention are found to provide protection from ischemia in the range of about 20 to 80%.

Example 14

Effects on Heart Ischemia/Reperfusion Injury in Rats

Female Sprague-Dawley rats, each weighing about 300–350 g are anesthetized with intraperitoneal ketamine at a dose of 150 mg/kg. The rats are endotracheally intubated and ventilated with oxygen-enriched room air using a Harvard rodent ventilator. Polyethylene catheters inserted into the carotid artery and the femoral vein are used for artery blood pressure monitoring and fluid administration respectively. Arterial $pCO_2$ is maintained between 35 and 45 mm Hg by adjusting the respirator rate. The rat chests are opened by median sternotomy, the pericardium. is incised, and the hearts are cradled with a latex membrane tent. Hemodynamic data are obtained at baseline after at least a 15-minute stabilization period following the end of the surgical operation. The LAD (left anterior descending) coronary artery is ligated for 40 minutes, and then re-perfused for 120 minutes. After 120 minutes' reperfusion, the LAD artery is re-occluded, and a 0.1 ml bolus of monastral blue dye is injected into the left atrium to determine the ischemic risk region.

The hearts are then arrested with potassium chloride and cut into five 2–3 mm thick transverse slices. Each slice is weighed and incubated in a 1% solution of trimethyltetrazolium chloride to visualize the infarcted myocardium located within the risk region. Infarct size is calculated by summing the values for each left ventricular slice and is further expressed as a fraction of the risk region of the left ventricle.

Various doses of the compounds of the invention are tested in this model. The compounds are given either in a single dose or a series of multiple doses, i.p. or i.v., at different times, both before or after the onset of ischemia. The compounds of the invention are found to have ischemia/reperfusion injury protection in the range of 10 to 40 percent. Therefore, they protect against ischemia-induced degeneration of rat hippocampal neurons in vitro.

Example 15

Retinal Ischemia Protection

A patient just diagnosed with acute retinal ischemia is immediately administered parenterally, either by intermittent or continuous intravenous administration, a compound of formula I, II, III, IV, V, VI, VII, or VIII, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects poststroke. In addition, it is expected that the re-occurrence of retinal ischemia would be prevented or reduced.

Example 16

Treatment of Retinal Ischemia

A patient has just been diagnosed with acute retinal ischemia. Immediately, a physician or a nurse parenterally administers a compound of formula I, II, III, IV, V, VI, VII, or VIII, either as a single dose or as a series of divided doses. The patient also receives the same or a different PARP inhibitor by intermittent or continuous administration via implantation of a biocompatible, biodegradable polymeric matrix delivery system comprising a compound of formula I, II, III, IV, V, VI, VII, or VIII, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of retinal ischemia would be reduced.

Example 17

Vascular Stroke Protection

A patient just diagnosed with acute vascular stroke is immediately administered parenterally, either by intermittent or continuous intravenous administration, a compound of formula I, II, III, IV, V, VI, VII, or VIII, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects poststroke. In addition, it is expected that the re-occurrence of vascular stroke would be prevented or reduced.

Example 18

Treatment of Vascular Stroke

A patient has just been diagnosed with acute multiple vascular strokes and is comatose. Immediately, a physician or a nurse parenterally administers a compound of formula I, II, III, IV, V, VI, VII, or VIII, either as a single dose or as a series of divided doses. Due to the comatose state of the patient, the patient also receives the same or a different PARP inhibitor by intermittent or continuous administration via implantation of a biocompatible, biodegradable polymeric matrix delivery system comprising a compound of formula I, II, III, IV, V, VI, VII, or VIII, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of vascular stroke would be reduced.

Example 19

Preventing Cardiac Reperfusion Injury

A patient is diagnosed with life-threatening cardiomyopathy and requires a heart transplant. Until a donor heart is found, the patient is maintained on Extra Corporeal Oxygenation Monitoring (ECMO).

A donor heart is then located, and the patient undergoes a surgical transplant procedure, during which the patient is placed on a heart-lung pump. The patient receives a compound of the invention intracardiac within a specified period of time prior to re-routing his or her circulation from the heart-lung pump to his or her new heart, thus preventing cardiac reperfusion injury as the new heart begins to beat independently of the external heart-lung pump.

Example 20

Septic Shock Assay

Groups of 10 C57/BL male mice weighing 18 to 20 g were administered a test compound, 1-carboxynaphthalene-1-carboxamide at the doses of 60, 20, 6 and 2 mg/kg, daily, by intraperitoneal (IP) injection for three consecutive days. Each animal was first challenged with lipopolysaccharide (LPS, from $E.\ Coli$, $LD_{100}$ of 20 mg/animal IV) plus galactosamine (20 mg/animal IV). The first dose of test compound in a suitable vehicle was given 30 minutes after challenge, and the second and third doses were given 24 hours later on day 2 and day 3 respectively, with only the surviving animals receiving the second or third dose of the test compound. Mortality was recorded every 12 hours after challenge for the three-day testing period. 1-Carboxynaphthalene-1-carboxamide provided a protection against mortality from septic shock of about 40%. Based on these results, other compounds of the invention are expected to provide a protection against mortality exceeding about 35%.

Example 21

Inhibition of PARP Activity

A patient has just been diagnosed with a disorder requiring the administration of a PARP inhibitor. A physician or a nurse parenterally administers a compound of formula I, II, III, IV, V, VI, VII, or VIII, either as a single dose or as a series of divided doses. The patient may receive the same or a different PARP inhibitor by intermittent or continuous administration via implantation of a biocompatible, biodegradable polymeric matrix delivery system comprising a compound of formula I, II, III, IV, V, VI, VII, or VIII, or via a subdural pump inserted to administer the compound directly to the desired treatment location. It would be expected that the treatment would alleviate the disorder, either in part or in its entirety and that no further occurrences of the disorder would develop.

Example 22

A treatment such as that described in Example 21 wherein the patient is diagnosed with a peripheral neuropathy caused by physical injury or a disease state.

Example 23

A treatment such as that described in Example 21 wherein the patient is diagnosed with Guillain-Barre syndrome.

Example 24

A treatment such as that described in Example 21 wherein the patient is diagnosed with traumatic brain injury.

Example 25

A treatment such as that described in Example 21 wherein the patient is diagnosed with physical damage to the spinal cord.

Example 26

A treatment such as that described in Example 21 wherein the patient is diagnosed with stroke associated with brain damage.

Example 27

A treatment such as that described in Example 21 wherein the patient is diagnosed with focal ischemia.

Example 28

A treatment such as that described in Example 21 wherein the patient is diagnosed with global ischemia.

Example 29

A treatment such as that described in Example 21 wherein the patient is diagnosed with reperfusion injury.

Example 30

A treatment such as that described in Example 21 wherein the patient is diagnosed with a demyelinating disease.

Example 31

A treatment such as that described in Example 21 wherein the patient is diagnosed with multiple sclerosis.

Example 32

A treatment such as that described in Example 21 wherein the patient is diagnosed with a neurological disorder relating to neurodegeneration.

Example 33

A treatment such as that described in Example 21 wherein the patient is diagnosed with Alzheimer's Disease.

Example 34

A treatment such as that described in Example 21 wherein the patient is diagnosed with Parkinson's Disease.

Example 35

A treatment such as that described in Example 21 wherein the patient is diagnosed with amyotrophic lateral sclerosis.

Example 36

A treatment such as that described in Example 21 wherein the patient is diagnosed with a cardiovascular disease.

Example 37

A treatment such as that described in Example 21 wherein the patient is diagnosed with angina pectoris.

Example 38

A treatment such as that described in Example 21 wherein the patient is diagnosed with myocardial infarction.

Example 39

A treatment such as that described in Example 21 wherein the patient is diagnosed with cardiovascular tissue damage related to PARP activation.

Example 40

In vitro Radiosensitization

The human prostate cancer cell line, PC-3s, were plated in 6 well dishes and grown at monolayer cultures in RPMII640 supplemented with 10% FCS. The cells are maintained at 37° C. in 5% $CO_2$ and 95% air. The cells were exposed to a dose response (0.1 mM to 0.1 uM) of 3 different PARP inhibitors of Formula I, II, III, IV, V, VI, VII, or VIII disclosed herein prior to irradiation at one sublethal dose level. For all treatment groups, the six well plates were exposed at room temperature in a Seifert 250 kV/15 mA irradiator with a 0.5 mm Cu/1 mm. Cell viability was examined by exclusion of 0.4% trypan blue. Dye exclusion was assessed visually by microscopy and viable cell number was calculated by subtracting the number of cells from the viable cell number and dividing by the total number of cells. Cell proliferation rates were calculated by the amount of $^3$H-thymidine incorporation post-irradiation. The PARP inhibitors show radiosensitization of the cells.

Example 41

In vivo Radiosensitization

Before undergoing radiation therapy to treat cancer, a patient is administered an effective amount of a compound or a pharmaceutical composition of the present invention. The compound or pharmaceutical composition acts as a radiosensitizer and making the tumor more susceptible to radiation therapy.

Example 42

Measuring Altered Gene Expression in mRNA Senescent Cells

Human fibroblast BJ cells, at Population Doubling (PDL) 94, are plated in regular growth medium and then changed to low serum medium to reflect physiological conditions described in Linskens, et al., *Nucleic Acids Res.* 23:16:3244–3251 (1995). A medium of DMEM/199 wupplemented with 0.5% bovine calf serum is used. The cells are treated daily for 13 days with the PARP inhibitor of Formula I, II, III, IV, V, VI, VII, or VIII as disclosed herein. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West, *Arch. Derm.* 130:87–95 (1994). Elastin expression of the cells treated with the PARP inhibitor of Formula I, II, III, IV, V, VI, VII, or VIII is significantly increased in comparison with the control cells. Elastin expression is significantly higher in young cells compared to senescent cells, and thus treatment with the PARP inhibitor of Formula I, II, III, IV, V, VI, VII, or VIII causes elastin expression levels in senescent cells to change to levels similar to those found in much younger cells. Similarly, a beneficial effect is seen in collagenase and collagen expression with treatment with the PARP inhibitors of Formula I, II, III, IV, V, VI, VII, or VIII.

Example 43

Measuring Altered Gene Expression Protein in Senescent Cells

Approximately 105 BJ cells, at PDL 95–100 are plated and grown in 15 cm dishes. The growth medium is DMEM/199 supplemented with 10% bovice calf serum. The cells are treated daily for 24 hours with the PARP inhibitors of Formula I, II, III, IV, V, VI, VII, or VIII (100 ug/1 mL of medium). The cells are washed with phosphate buffered solution (PBS), then permeablized with 4% paraformaldehyde for 5 minutes, then washed with PBS, and treated with 100% cold methanol for 10 minutes. The methanol is removed and the cells are washed with PBS, and then treated with 10% serum to block nonspecific antibody binding. About 1 mL of the appropriate commercially available antibody solutions (1:500 dilution. Vector) is added to the cells and the mixture incubated for 1 hour. The cells are rinsed and washed three times with PBS. A secondary antibody, goat anti-mouse IgG (1 mL) with a biotin tag is added along with 1 mL of a solution containing streptavidin conjugated to alkaline phosphatase and 1 mL of NBT reagent (Vector). The cells are washed and changes in gene expression are noted calorimetrically. Four senescence-specific genes—collagen I, collagen III, collagenase, and interferon gamma—in senescent cells treated with the PARP inhibitor of Formula I, II, III, IV, V, VI, VII, or VIII are monitored and the results show a decrease in interferon gamma expression with no observable change in the expression levels of the other three gens, demonstrating that the PARP inhibitors of Formula I, II, III, IV, V, VI, VII, or VIII can alter senescence-specific gene expression.

Example 44

Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per $cm^2$ in 6-well tissue culture plates in DMEM/199 medium supplemented with 10% bovine calf serum and varying amounts (0.10 uM, and 1 mM: from a 100×stock solution in DMEM/M199 medium) of a PARP inhibitor of Formula I, II, III, IV, V, VI, VII, or VIII as disclosed herein. This process is repeated every 7 days until the cell appear to stop dividing. The untreated (control) cells reach senescence and stop dividing after about 40 days in culture. Treatment of cells with 10 uM 3-AB appears to have little or no effect in contrast to treatment with 100 uM 3-AB which appears lengthen the lifespan of the cells and treatment with 1 mM 3-AB which dramatically increases the lifespan and proliferative capacity of the cells. The cells treated with 1 mM 3-AB will still divide after 60 days in culture.

Example 45

Neuroprotective Effects of Formula I, II, III, IV, V, VI, VII, or VIII on Chronic Constriction Injury (CCI) in Rats Adult male Sprague-Dawley rats, 300–350 g, are anesthetized with intraperitoneal 50 mg/kg sodium pentobarbital. Nerve ligation is performed by exposing one side of the rat's sciatic nerves and dissecting a 5–7 mm-long nerve segment and closing with four loose ligatures at a 1.0–1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hyperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-withdrawal latency is defined as the time elapsed from the onset of radiant heat stimulation to withdrawal of the rat's hindpaw.

Mechanical hyperalgesia is assessed by placing the rat in a cage with a bottom made of perforated metal sheet with many small square holes. Duration of paw-withdrawal is recorded after pricking the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I–II, of rats 8 days after unilateral sciatic nerve ligation as compared with sham operated rats. Various doses of differing compounds of Formula I, II, III, IV, V, VI, VII, or VIII are tested in this model and show that the Formula I, II, III, IV, V, VI, VII, or VIII compounds reduce both incidence of dark neurons and neuropathic pain behavior in CCI rats.

The invention being thus described, it will be obvious that the same may be varied in many ways. Such variations are not to be regarded as a departure from the spirit and scope of the invention, and all such modifications are intended to be included within the scope of the following claims.

We claim:

1. A compound having an $IC_{50}$ of 25 $\mu$M or lower for inhibiting poly(ADP-ribose)polymerase in vitro, said compound being a compound of formula I:

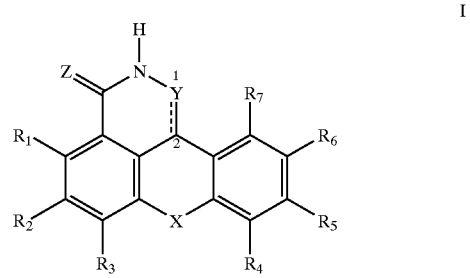

or a pharmaceutically acceptable salt, hydrate, prodrug, or mixtures thereof, wherein Y is $C_1$ alkylhalo, $C_1$ alkyl-CO—G, a direct bond, C=O, or $CR_8$;

G is $NR_{11}R_{16}$, $OR_9$, $SR_9$, or $R_{10}$;

Z is O, S, or $NR_{11}$;

X is O;

$R_1$, $R_2$, $R_3$, $R_4$, $R_5$, $R_6$, $R_7$, $R_8$, $R_{10}$, $R_{12}$, $R_{13}$, $R_{14}$, or $R_{15}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, nitro, nitroso, carboxy, or aralkyl;

$R_9$ is hydrogen, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

$R_{11}$ or $R_{16}$ are independently: hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, aryl, amino, alkylamino, carboxy, or aralkyl;

with the provisos that when Y is $CR_8$ then $R_8$ is halo, hydroxy, amino, alkylamino, nitro, nitroso, carboxy or aralkyl; and that when Y is $CR_8$ and Z is O, then at least one of $R_1$, $R_2$, $R_3$, $R_4$, $R_5$, $R_6$, and $R_7$, and $R_8$ are selected from the group consisting of halo, aryl, amino, alkylamino, nitro, nitroso, carboxy or aralkyl, and $R_1$, $R_2$, $R_3$, $R_4$, $R_5$, $R_6$, $R_7$ or $R_8$ are not phenyl; and further wherein said alkyl, alkenyl, cycloalkyl, cycloalkenyl, aryl and aralkyl groups are independently substituted with one or more substituent(s) selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and aryl having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy; with the provisos that Y is not $CR_8$ when there is a double bond between $C_1$ and $C_2$ and that when Z is oxygen and $R_1$–$R_7$ are hydrogen then Y is not a direct bond.

2. A compound selected from the group consisting of

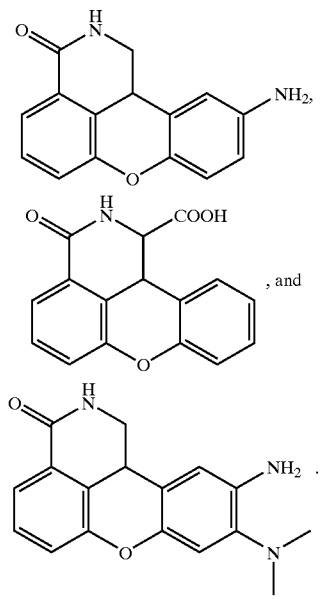

3. A pharmaceutical composition comprising a compound of claim 1 and a pharmaceutically acceptable carrier.

4. The pharmaceutical composition of claim 3, wherein the carrier is a sterile solution, suspension or emulsion, in a single or divided dose.

5. The pharmaceutical composition of claim 3, wherein the carrier is a capsule or tablet containing a single or divided dose of said compound.

6. The pharmaceutical composition of claim 3, wherein the carrier comprises a biodegradable polymer.

7. The pharmaceutical composition of claim 6, wherein the biodegradable polymer releases the compound of formula I over a prolonged period of time.

8. The pharmaceutical composition of claim 3, wherein the carrier is a solid implant.

9. A method of inhibiting PARP activity, extending or increasing the proliferative capacity of cells, altering gene expression of senescent cells, or radiosensitizing tumor cells, in an animal comprising: administering a therapeutically effective amount of a compound of claim 1 to said animal.

10. A method of inhibiting PARP activity, extending or increasing the proliferative capacity of cells, altering gene expression of senescent cells, or radiosensitizing tumor cells, in an animal comprising: administering a therapeutically effective amount of a compound of claim 2 to said animal.

11. The method of claim 9 further comprising treating diseases or disorders selected from the group consisting of tissue damage resulting from cell damage or death due to necrosis or apoptosis, neuronal mediated tissue damage or diseases, neural tissue damage resulting from ischemia and reperfusion injury, neurological disorders and neurodegenerative diseases, vascular stroke, cardiovascular disorders, age-related macular degeneration, AIDS, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock, and skin aging, diseases or disorders relating to lifespan or proliferative capacity of cells, and diseases or disease conditions induced or exacerbated by cellular senescence.

12. The method of claim 11, wherein the neurological disorder is selected from the group consisting of peripheral neuropathy caused by physical injury or disease state, traumatic brain injury, physical damage to the spinal cord, stroke associated with brain damage, and demyelinating diseases.

13. The method of claim 12, wherein the peripheral neuropathy is caused by Guillain-Barre syndrome.

14. The method of claim 12, wherein the demyelinating disease is multiple sclerosis.

15. The method of claim 11, wherein the neurodegenerative disease is selected from the group consisting of Alzheimer's Disease, Parkinson's Disease, Huntington's Disease and amyotropic lateral sclerosis.

16. The method of claim 11, wherein the cancer is selected from the group consisting of ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

17. The method of claim 11, wherein the bowel disorder is colitis.

18. The method of claim 11, wherein the bowel disorder is Crohn's disease.

19. The method of claim 11, wherein the cardiovascular disorder is selected from the group consisting of cardiovascular tissue damage, coronary artery disease, myocardial infarction, angina pectoris and cardiogenic shock.

20. The method of claim 11, wherein the septic shock is endotoxic shock.

21. The method of claim 11, wherein the disease or disease condition induced or exacerbated by cellular senescence is selected from the group consisting of skin aging, Alzheimer's disease, atherosclerosis, osteoarthritis, osteoporosis, muscular dystrophy, age-related macular degeneration, immune senescence, and AIDS.

* * * * *